United States Patent
Monson

(10) Patent No.: US 11,590,227 B2
(45) Date of Patent: Feb. 28, 2023

(54) SAPOSIN C PHARMACEUTICAL COMPOSITIONS AND METHODS OF TREATING CANCER

(71) Applicant: Bexion Pharmaceuticals Inc., Covington, KY (US)

(72) Inventor: Ellen K. Monson, Cincinnati, OH (US)

(73) Assignee: Bexion Pharmaceuticals, Inc., Covington, KY (US)

( * ) Notice: Subject to any disclaimer, the term of this patent is extended or adjusted under 35 U.S.C. 154(b) by 0 days.

(21) Appl. No.: 16/865,168

(22) Filed: May 1, 2020

(65) Prior Publication Data
US 2020/0384112 A1 Dec. 10, 2020

Related U.S. Application Data

(62) Division of application No. 16/179,139, filed on Nov. 2, 2018, now Pat. No. 10,682,411.

(60) Provisional application No. 62/678,668, filed on May 31, 2018, provisional application No. 62/647,058, filed on Mar. 23, 2018.

(51) Int. Cl.
| | | |
|---|---|---|
| *A61K 47/12* | (2006.01) | |
| *C07K 14/47* | (2006.01) | |
| *A61P 35/00* | (2006.01) | |
| *A61K 47/10* | (2017.01) | |
| *A61K 47/18* | (2017.01) | |
| *A61K 47/26* | (2006.01) | |
| *A61K 47/24* | (2006.01) | |
| *A61K 9/00* | (2006.01) | |
| *A61K 9/127* | (2006.01) | |
| *A61K 38/18* | (2006.01) | |
| *A61K 9/19* | (2006.01) | |
| *C12Q 1/40* | (2006.01) | |

(52) U.S. Cl.
CPC ............ *A61K 47/12* (2013.01); *A61K 9/0019* (2013.01); *A61K 9/127* (2013.01); *A61K 9/19* (2013.01); *A61K 38/18* (2013.01); *A61K 47/10* (2013.01); *A61K 47/18* (2013.01); *A61K 47/24* (2013.01); *A61K 47/26* (2013.01); *A61P 35/00* (2018.01); *C07K 14/4705* (2013.01); *C12Q 1/40* (2013.01); *C12Q 2334/22* (2013.01)

(58) Field of Classification Search
None
See application file for complete search history.

(56) References Cited

U.S. PATENT DOCUMENTS

| | | |
|---|---|---|
| 4,162,282 A | 7/1979 | Fulwyler et al. |
| 4,310,505 A | 1/1982 | Baldeschwieler et al. |
| 4,533,254 A | 8/1985 | Cook et al. |
| 4,728,575 A | 3/1988 | Gamble et al. |
| 4,728,578 A | 3/1988 | Higgins et al. |
| 4,737,323 A | 4/1988 | Martin et al. |
| 4,921,706 A | 5/1990 | Roberts et al. |
| 5,205,290 A | 4/1993 | Unger |
| 6,872,406 B2 | 3/2005 | Qi |
| 7,834,147 B2 * | 11/2010 | Qi .......................... A61P 43/00 530/300 |
| 9,271,932 B2 | 3/2016 | Qi |
| 9,757,432 B2 | 9/2017 | Kaur et al. |
| 2010/0311844 A1 | 12/2010 | Qi et al. |
| 2017/0002013 A1 * | 1/2017 | Krainc ........... C12Y 302/01045 |
| 2018/0051315 A1 * | 2/2018 | Bernhardt ...... C12Y 302/01045 |
| 2018/0169120 A1 | 6/2018 | Qi et al. |

FOREIGN PATENT DOCUMENTS

| | | |
|---|---|---|
| CN | 1735424 A | 2/2006 |
| CN | 101209251 A | 7/2008 |
| CN | 101541307 A | 9/2009 |
| CN | 102614125 A | 8/2012 |
| GB | 2193095 | 2/1988 |
| RU | 2266129 C2 | 12/2005 |
| WO | WO2007/127439 | 11/2007 |
| WO | WO2014/078522 | 5/2014 |
| WO | WO2018/094406 | 5/2018 |

OTHER PUBLICATIONS

Tamargo et al., "The role of saposin C in Gaucher disease," Molecular Genetics and Metabolism, Jul. 2012, 106(3):257-263.
Abu-Baker et al., "Cytotoxicity and Selectivity in Skin Cancer by SapC-DOPS Nanovesicles," J Cancer Ther (Aug. 2012); 3(4):321-326.
Abu-Baker et al., "Investigating the Interaction of Saposin C with POPS and POPC Phospholipids: A Solid-State NMR Spectroscopic Study," Biophysical Journal, vol. 93:3480-3490 (Nov. 2007).
Bexion, Phase 1 Study of BXQ-350 in Adult Patients with Advanced Solid Tumors, Study version 6; submitted to ClinicalTrials.gov on Dec. 20, 2017; downloaded from ClinicalTrials.gov archive on Aug. 26, 2019 as https://clinicaltrials.gov/ct2/history/NCT02859857?V_6=View (13 pages).
Bexion, Phase 1 Study of BXQ-350 in Adult Patients with Advanced Solid Tumors, Study version 9; submitted to ClinicalTrials.gov on Aug. 23, 2018; downloaded from ClinicalTrials.gov archive on Aug. 26, 2019 as https://clinicaltrials.gov/ct2/history/NCT02859857?V_9=View (12 pages).
Blanco et al., "Phosphatidylserine-selective targeting and anticancer effects of SapC-DOPS nanovesicles on brain tumors," Oncotarget, Advance Publications 2014, pp. 1-14 (Jul. 14, 2014).
Blanco et al., "SapC-DOPS nanovesicles: a novel targeted agent for the imaging and treatment of glioblastoma," Oncoscience 2015, 2(2): 1-9 (Feb. 2015).

(Continued)

*Primary Examiner* — Nghi V Nguyen
(74) *Attorney, Agent, or Firm* — FisherBroyles, LLP; Christy G. Rothwell

(57) ABSTRACT

Disclosed are pharmaceutical compositions containing saposin C and phosphatidylserine that are useful for treating various cancers. Also disclosed are methods for assaying potency of a test composition comprising saposin C and an anionic phospholipid.

20 Claims, 23 Drawing Sheets

Specification includes a Sequence Listing.

(56) References Cited

OTHER PUBLICATIONS

Blanco et al., "Imaging and Therapy of Pancreatic Cancer with Phosphatidylserine-Targeted Nanovesicles," Translational Oncology, 8(3)496-203 (Jun. 2015).

Chen et al., "An overview of liposome lyophilization and its future potential," Journal of Controlled Release, 142(3):299-311, Mar. 1, 2010.

Cheng et al., "The production and evaluation of contrast-carrying liposomes made with an automatic high-pressure system," Invest Radiol, Jan. 1987; 22(1)47-55.

Chu et al., "Targeting and cytotoxicity of SapC-DOPS nanovesicles in pancreatic cancer," PLoS One, Oct. 2013; 8(10):e75507 (pp. 1-11).

Chu et al., "Saposin C: Neuronal Effect and CNS Delivery by Liposomes," Ann. N.Y. Acad. Sci. 1053:237-246 (2005).

Davis et al., "Enhanced phosphatidylserine-selective cancer therapy with irradiation and SapC-DOPS nanovesicles," Oncotarget, 10(8):856-868 (Jan. 25, 2019).

Hope et al., "Production of large unilamellar vesicles by a rapid extrusion procedure: characterization of size distribution, trapped volume and ability to maintain a membrane potential," Biochimica et Biophysica Acta, 1985; 812(1):55-65.

Kishimoto et al., "Saposins: structure, function, distribution, and molecular genetics," Journal of Lipid Research, 1992, 33:1255-1267.

Madden et al., "The accumulation of drugs within large unilamellar vesicles exhibiting a proton gradient: a survey," Chemistry and Physics of Lipids, 1990; 53:37-46.

Mayhew et al., "Characterization of liposomes prepared using a microemulsifier," Biochimica et Biophysica Acta, 1984; 755(2):169-174.

Mayhew et al., "High-pressure continuous-flow system for drug entrapment in liposomes," Methods in Enzymology, 1987;149:64-77.

Nieh et al., "Controlled release mechanisms of spontaneously forming unilamellar vesicles," Biochimica et Biophysica Acta (2008) 1778:1467-1471.

Olowokure et al., "Pancreatic cancer: current standards, working towards a new therapeutic approach," Expert Rev. Anticancer Ther. Early online, informahealthcare.com, pp. 1-3 (2014) DOI: 10.1586/14737140.2014.895937.

Qi et al., "Cancer-selective targeting and cytotoxicity by liposomal-coupled lysosomal saposin C protein," Clin Cancer Res, Sep. 2009; 15(18):5840-5851 DOI: 10.1158/1078-0432.CCR-08-3285.

Qi et al., " Functional organization of saposin C. Definition of the neurotrophic and acid beta-glucosidase activation regions," J. Biol, Chem., Mar. 1996; 271(12):6874-6880.

Qi et al., "Functional Human Saposins Expressed in *Escherichia coli*, Evidence for Binding and Activation Properties of Saposins C with Acid β-Glucosidase," The Journal of Biological Chemistry, vol. 269, No. 24, p. 16746-16753 (Jun. 17, 1994).

Qi et al., "Differential Membrane Interactions of Saposins A and C," The Journal of Biological Chemistry, vol. 276, No. 29, pp. 27010-27017 (2001).

Qi et al., "Ex vivo localization of the mouse saposin C activation region for acid β-glucosidase," Molecular Genetics and Metabolism (2002) 76:189-200.

Sampreeti et al., "Effects of Excipient Interactions on the State of the Freeze-Concentrate and Protein Stability," Pharmaceutical Research, 34(2)462-478, Dec. 15, 2016.

Sulaiman et al., "SapC-DOPS nanovesicles induce Smac-and Bax-dependent apoptosis through mitochondrial activation in neuroblastomas," Molecular Cancer (2015) 14:78, pp. 1-15 doi: 10.1186/s12943-015-0336-y.

Vaccaro et al., "Saposin C induces pH-dependent destabilization and fusion of phosphatidylserine-containing vesicles," FEBS Letters (1994) 349:181-186.

Vaccaro et al., "Structural Analysis of Saposin C and B, Complete Localization of Disulfide Bridges," The Journal of Biological Chemistiy (1995); 270(17):9953-9960.

Vaccaro et al., "pH-dependent Conformational Properties of Saposins and Their Interactions with Phospholipid Membranes," The Journal of Biological Chemistry (1995); 270(51):30576-30580.

Vaccaro et al., "Saposins and Their Interaction with Lipids," Neurochemical Research (1999) 24(2):307-314.

Wang et al., "Phospholipid vesicle fusion induced by saposin C," Archives of Biochemistry and Biophysics (2003) 415:43-53 doi: 10.1016/S0003-9861(03)00219-4.

Wojton et al., "SapC-DOPS-induced lysosomal cell death synergizes with TMZ in glioblastoma," Oncotarget, Advance Publications 2014, pp. 1-7 (Jul. 17, 2014).

Wojton et al., "Systematic delivery of SapC-DOPS has antiangiogenic and antitumor effects against glioblastoma," Mol Ther, Aug. 2013; 21:1517-1525 doi: 10.1038/mt.2013.114.

You et al., "Phospholipid Membrane Interactions of Saposin C: In Situ Atomic Force Microscopic Study," Biophysical Journal (Mar. 2003) 84:2043-2057.

Zhao et al., "SapC-DOPS Nanovesicles as Targeted Therapy for Lung Cancer," Molecular Cancer Therapeutics, 2015; 14(2):491-498 doi: 10.1158/1535-7163.MCT-14-0661.

International Search Report and Written Opinion in related Application No. PCT/US2018/059016, dated Feb. 22, 2019, 16 pages.

Casal et al., "Infrared and 31P-NMR studies of the effect of Li+ and Ca2+ on phosphatidylserines," Biochimica et Biophysica Acta, Jun. 23, 1987, 919(3):275-286.

Frankel et al., "Characterization of diphtheria fusion proteins targeted to the human interleukin-3 receptor," Protein Engineering, Design and Selection, Aug. 1, 2000, 13(8):575-581.

Konstantino et al., "Damage to Lyophilized Protein Preparations: A Survey," Biokhimiya, 1998, 63(3):422-429 (with English abstract).

Liu et al., "Role of lysine residues in membrane anchoring of saposin C," Archives of Biochemistry and Biophysics, Nov. 15, 2005, 443(1-2):101-112.

Muller et al., "Spliceosomal peptide P140 for immunotherapy of systemic lupus erythematosus: Results of an early phase II clinical trial," Arthritis & Rheumatism: Official Journal of the American College of Rheumatology, Dec. 2008, 58(12):3873-3883.

Nieh et al., "Spontaneously Forming Ellipsoidal Phospholipid Unilamellar Vesicles and Their Interactions with Helical Domains of Saposin C," Langmuir, Nov. 2, 2006, 22(26):11028-11033.

Pakula et al., "Genetic analysis of protein stability and function," Annual Review of Genetics, Dec. 1989, 23:289-310.

RU Office Action and Search Report in Russian Appln. No. 2020134655, dated Mar. 17, 2021, 33 pages (with English translation).

Tokuriki et al., "Stability effects of mutations and protein evolvability," Current Opinion in Structural Biology, Oct. 1, 2009, 19(5):596-604.

Yang et al., "High-level expression and deletion mutagenesis of human tryptophan hydroxylase," Proc. Natl. Acad. Sci. USA, Jul. 5, 1994, 91(14):6659-6663.

Extended European Search Report in European Appln. No. 21192293.5, dated May 3, 2022, 9 pages.

* cited by examiner

| DOSE (mg/kg) | 0.7 | 1.1 | 1.4 | 1.8 | 2.4 |
|---|---|---|---|---|---|
| N | 1 | 3 | 3 | 3 | 8 |
| Mean Age | 64 | 53 | 58 | 49 | 54 |
| F:M | 0:1 | 0:3 | 2:1 | 1:2 | 2:2 |
| Solid Tumor | 0 | 2 | 1 | 1 | 5 |
|    Improved RANO (n/NDY113) Partial Response | 1/1 | 1/1 | 1/2 | - | - |
| HGG | 1 | 1 | 2 | 2 | 3 |
|    Improved RECIST (n/NDY113) | 1/1 | | | | 2/2 |
| Non-related Discontinuation | | 3 | 3 | 2 | 7 |
| Adverse Events (*n Cases, n Events*) | 1,15 | 3,54 | 3,37 | 3,32 | 8,80 |
| Moderate Severity, Related | | 3,6 | 1,1 | 1,2 | 2,2 |
|    Fatigue | | 2,2 | | 1,2 | 1,1 |
|    Neutropenia | | 1,1 | | | |
|    EKG | | 1,2 | | | |
|    Balance | | 1,1 | | | |
|    Nervous | | 1,1 | | | |
|    Dysarthria | | 1,1 | | | |
|    Urinary | | | 1,1 | | |
|    BP | | | | | 1,1 |
| Serious, Non-related | 1,1 | 1,4 | 1,3 | 1,3 | 3,5 |
|    GI | | 1,1 | 1,1 | | 1,3 |
|    Hyponatremia | | 1,1 | | | |
|    Weakness | | | 1,1 | | |

HGG: High Grade Glioma, RECIST: Response Evaluation Criteria in Solid Tumors, RANO: Response Assessment in Neuro-onocology Criteria

FIG. 26

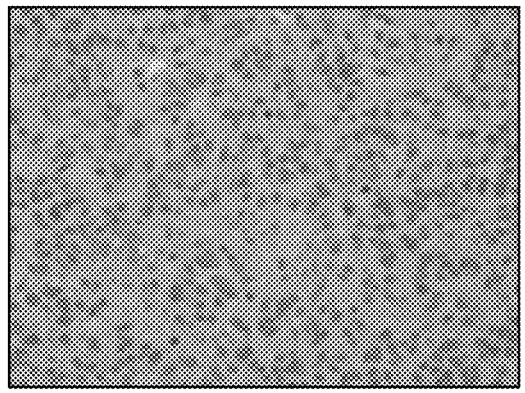
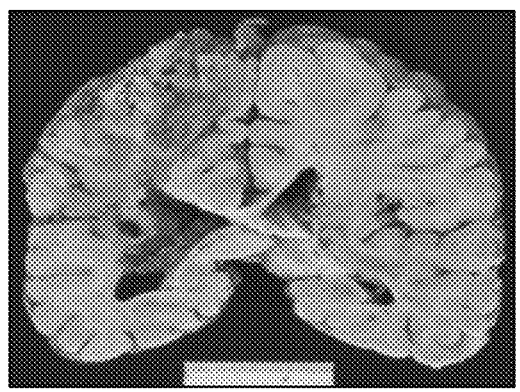
FIG. 28A                FIG. 28B
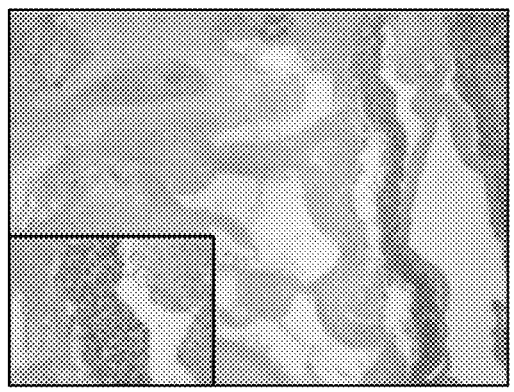
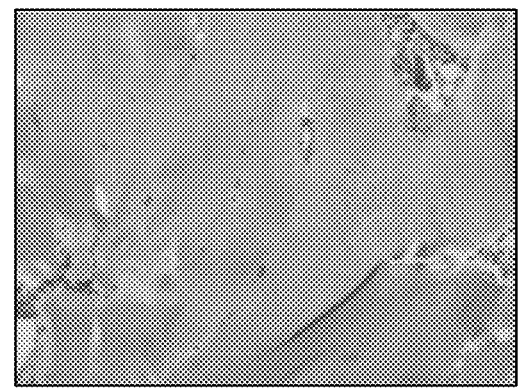
FIG. 28C                FIG. 28D

SEQUENCE LISTING

<160> NUMBER OF SEQ ID NOS: 1

<210> SEQ ID NO 1
<211> LENGTH: 80
<212> TYPE: PRT
<213> ORGANISM: Homo sapiens

<400> SEQUENCE: 1

Ser Asp Val Tyr Cys Glu Val Cys Glu Phe Leu Val Lys Glu Val Thr
1               5                   10                  15

```
Lys Leu Ile Asp Asn Asn Lys Thr Glu Lys Glu Ile Leu Asp Ala Phe
            20              25              30

Asp Lys Met Cys Ser Lys Leu Pro Lys Ser Leu Ser Glu Glu Cys Gln
        35              40              45

Glu Val Val Asp Thr Tyr Gly Ser Ser Ile Leu Ser Ile Leu Leu Glu
    50              55              60

Glu Val Ser Pro Glu Leu Val Cys Ser Met Leu His Leu Cys Ser Gly
65              70              75              80
```

SAPOSIN C PHARMACEUTICAL COMPOSITIONS AND METHODS OF TREATING CANCER

CROSS-REFERENCE TO RELATED APPLICATIONS

This application is a divisional of U.S. application Ser. No. 16/179,139, filed on Nov. 2, 2018, and issued as U.S. Pat. No. 10,682,411, which claims the benefit of U.S. Provisional Application No. 62/647,058, filed on Mar. 23, 2018, and U.S. Provisional Application No. 62/678,668, filed on May 31, 2018.

STATEMENT REGARDING GOVERNMENT-FUNDED RESEARCH

This invention was made with Federal government support under contract numbers 2R44CA136017-02A1, 5R44CA136017-03, and 2R44CA136017-04, awarded by the National Institutes of Health. The Federal government has certain rights in the invention.

This invention was made with an award from the Kentucky Cabinet for Economic Development, Department of Commercialization and Innovation, under Grant Agreement KSTC-184-512-11-100 with the Kentucky Science and Technology Corporation.

FIELD OF THE INVENTION

The present invention relates to compositions containing saposin C and methods of using them to treat various cancer conditions.

SEQUENCE LISTING

This application contains a Sequence Listing that has been submitted electronically as an ASCII text file named SequenceListing.txt. The ASCII text file, created on May 1, 2020, is 1.09 kilobytes in size. The material in the ASCII text file is hereby incorporated by reference in its entirety.

BACKGROUND

Saposins, a family of small (~80 amino acids) heat stable glycoproteins, are essential for the in vivo hydrolytic activity of several lysosomal enzymes in the catabolic pathway of glycosphingolipids. Saposins A, B, C, and D are described in U.S. Pat. Nos. 7,834,147 and 9,271,932.

Nanovesicles comprising saposin C ("SapC") and dioleoyl phosphatidylserine (DOPS) have high affinity for phosphatidylserine-rich membranes in vitro and in vivo, and can induce apoptosis and/necrosis in target cells (Qi et al. (2009), Clin Cancer Res 2009; 15: 5840-5851). The proposed mechanism by which the SapC-DOPS nanovesicles induce apoptosis is via ceramide elevation through activation of β-glucosidase and acid sphingomyelinase (with subsequent degradation of glucosylceramide and sphingomyelin, respectively), which leads to activation of caspases. The nanovesicle preparation was found to be efficacious against a wide variety of tumor types in vitro and in orthotopic murine tumor models (Qi et al. (2009); Wojton et al. (2013), Mol Ther, 21: 1517-1525; Abu-Baker et al. (2012), J Cancer Ther, 3: 321-326; Chu et al. (2013), PLoS One; 8: e75507; U.S. Pat. No. 7,834,147).

SUMMARY

This disclosure pertains to aqueous and solid compositions comprising saposin C and methods of using such compositions in the treatment of cancer.

A composition is described that includes: a polypeptide including the amino acid sequence of SEQ ID NO: 1 with zero to four amino acid insertions, substitutions, or deletions; a phosphatidylserine lipid; a buffer at pH 5.0 to 8.0; trehalose at 1.5 to 9 percent w/w; t-butyl alcohol at 0 to 35 percent; and water. The polypeptide is at a concentration of 0.4 to 5.0 mg/ml, and the molar ratio of the phosphatidylserine lipid to the polypeptide is in the range of 8:1 to 20:1. In some embodiments, the buffer is tris(hydroxymethyl)aminomethane (Tris) at a concentration of 10 to 50 mM, and the pH of the composition is pH 6.8 to 7.6. In some embodiments, the buffer is citrate buffer at a concentration of 10 to 50 mM. In some embodiments, the buffer is acetate buffer at a concentration of 10 to 50 mM. In certain embodiments, the phosphatidylserine lipid comprises one or more of dioleoyl phosphatidylserine (DOPS), dihexanoyl phosphatidylserine lipid, dioctanoyl phosphatidylserine lipid, didecanoyl phosphatidylserine lipid, dilauroyl phosphatidylserine lipid, dimyristoyl phosphatidylserine lipid, dipalmitoyl phosphatidylserine lipid, palmitoyl-oleoyl phosphatidylserine lipid, 1-stearoyl-2-oleoyl phosphatidylserine lipid, or diphytanoyl phosphatidylserine lipid. The phosphatidylserine lipid is preferably DOPS, which may be in the form of a salt such as a sodium salt. In various cases, the polypeptide includes or consists of amino acid sequence of SEQ ID NO: 1 or the sequence of SEQ ID NO:1 with one or two amino acid insertions, substitutions, or deletions. In a preferred embodiment, the composition includes: a polypeptide including the amino acid sequence of SEQ ID NO: 1, at a concentration of 1.9 to 2.5 mg/ml; DOPS at a concentration of 2.0 to 2.8 mg/ml; Tris at a concentration of 23 to 27 mM; trehalose at a concentration of 4 to 6 percent w/w; and t-butyl alcohol at a concentration of about 15 to 25 percent w/w; with pH in the range of pH 6.8 to 7.6.

Also described is a composition in solid form, e.g., a lyophilized powder composition, that includes: a polypeptide including the amino acid sequence of SEQ ID NO: 1 with zero to four amino acid insertions, substitutions, or deletions; a phosphatidylserine lipid; a buffer; and trehalose at 75 to 90 percent w/w. The polypeptide in this composition is at a concentration of 3.2 to 4.4 percent w/w, and the molar ratio of phosphatidylserine lipid to polypeptide is in the range of 8:1 to 20:1. In some embodiments, the buffer is Tris at 5.6 to 7.6 percent w/w. In some embodiments, the buffer is citrate buffer at 9 to 13 percent w/w. In some embodiments, the buffer is acetate buffer at 3 to 5 percent w/w. In certain embodiments, the phosphatidylserine lipid includes one or more of dioleoyl phosphatidylserine (DOPS), dihexanoyl phosphatidylserine lipid, dioctanoyl phosphatidylserine lipid, didecanoyl phosphatidylserine lipid, dilauroyl phosphatidylserine lipid, dimyristoyl phosphatidylserine lipid, dipalmitoyl phosphatidylserine lipid, palmitoyl-oleoyl phosphatidylserine lipid, 1-stearoyl-2-oleoyl phosphatidylserine lipid, or diphytanoyl phosphatidylserine lipid. In various cases, the composition includes or consists of the polypeptide amino acid sequence of SEQ ID NO: 1, or includes the sequence of SEQ ID NO:1 with one or two amino acid insertions, substitutions, or deletions. In some embodiments, this composition includes t-butyl alcohol in an amount less than 3 percent w/w. In a preferred embodiment, the solid composition includes: a polypeptide including the amino acid sequence of SEQ ID NO: 1 at a concentration of 3.3 to 4.3 percent w/w; DOPS (e.g., the sodium salt) at a concentration of 3.4 to 4.8 percent w/w; Tris at a concentration of 6.0 to 7.2 percent w/w; trehalose at a concentration of 81 to 87.3 percent w/w; and t-butyl alcohol at a concentration of less than 3 percent w/w.

Also described is a pharmaceutical composition that includes: a polypeptide including the amino acid sequence of SEQ ID NO: 1 with zero to four amino acid insertions, substitutions, or deletions; a phosphatidylserine lipid; a buffer at pH 5.0 to 8; trehalose at 1.5 to 9 percent w/v; and water. The polypeptide is at a concentration of 0.4 to 5 mg/ml, and the molar ratio of phosphatidylserine lipid to polypeptide is in the range of 8:1 to 20:1. In some embodiments, the buffer is Tris at a concentration of 10 to 50 mM, and the pH of the composition is pH 6.8 to 7.6. In some embodiments, the buffer is citrate buffer at a concentration of 10 to 50 mM. In some embodiments, the buffer is acetate buffer at a concentration of 10 to 50 mM. In certain embodiments, the phosphatidylserine lipid comprises one or more of DOPS, dihexanoyl phosphatidylserine lipid, dioctanoyl phosphatidylserine lipid, didecanoyl phosphatidylserine lipid, dilauroyl phosphatidylserine lipid, dimyristoyl phosphatidylserine lipid, dipalmitoyl phosphatidylserine lipid, palmitoyl-oleoyl phosphatidylserine lipid, 1-stearoyl-2-oleoyl phosphatidylserine lipid, or diphytanoyl phosphatidylserine lipid, and preferably is DOPS, e.g., the sodium salt of DOPS. In various cases, the polypeptide comprises or consists of the amino acid sequence of SEQ ID NO: 1, or comprises or consists of the sequence of SEQ ID NO:1 with one or two amino acid insertions, substitutions, or deletions. In some embodiments, this composition includes t-butyl alcohol in an amount less than 3 percent. In a preferred embodiment, the composition includes: a polypeptide including the amino acid sequence of SEQ ID NO: 1 at a concentration of 1.9 to 2.5 mg/ml; DOPS (preferably in its sodium salt form) at a concentration of 2.0 to 2.8 mg/ml; Tris at a concentration of 23 to 27 mM; trehalose at a concentration of 4 to 6 percent w/w; t-butyl alcohol in an amount less than 0.5 percent w/w; with pH in the range of pH 6.8 to 7.6 (more preferably pH 7.0 to 7.4, or pH 7.1 to 7.3). Also described is a method for treating cancer, which may be a solid tumor. Examples of cancers treatable in the method include glioma, ependymoma, and gastrointestinal cancer such as rectal adenocarcinoma. The method includes administering to a human cancer patient a pharmaceutical composition described herein. In some embodiments, the method includes reconstituting the solid composition described herein in water or saline to produce a reconstituted composition, and intravenously administering a dose of the reconstituted composition to the patient. In some embodiments, the composition is delivered intravenously in a dose ranging from 0.4 mg/kg to 7 mg/kg SapC, and the ratio of SapC to DOPS in the composition is in the range of 1.8 to 1:20. In another embodiment, the composition is delivered intravenously in a dose of 2.3-2.5 mg/kg SapC, and the ratio of SapC to DOPS in the composition is in the range of 1:11 to 1:13. In some embodiments, the composition is administered repeatedly to the patient over at least two cycles, as follows:

Cycle 1:
week 1: one dose on each of days 1-5;
week 2: 3×/week every other day, e.g. one dose on each of days 8, 10, and 12;
weeks 3 and 4: one dose each week (every 7 (+/−3) days);
Cycle 2:
one dose during week 5; and
any subsequent cycle:
one dose 28 (+/−3) days after the most recent prior dose.

BRIEF DESCRIPTION OF THE DRAWINGS

FIG. 26 is a table showing Phase 1a demographics and adverse events by dosing group.

FIGS. 28A-D are depictions of results from post-mortem histology and gross anatomy analysis; from left to right: (A) The initial surgical specimen showed little evidence of ependymal differentiation and abundant mitotic figures. H&E at 40×; (B) Gross brain examination at autopsy showed extensive tumor necrosis; (C) Microscopic examination of sections of tumor shows little viable tumor and necrosis (H&E at 4× with insert at 40×); (D) At autopsy there was extensive chondroid differentiation at the site where tumor extended through the surgical defect and scalp.

DETAILED DESCRIPTION

Figure 1:
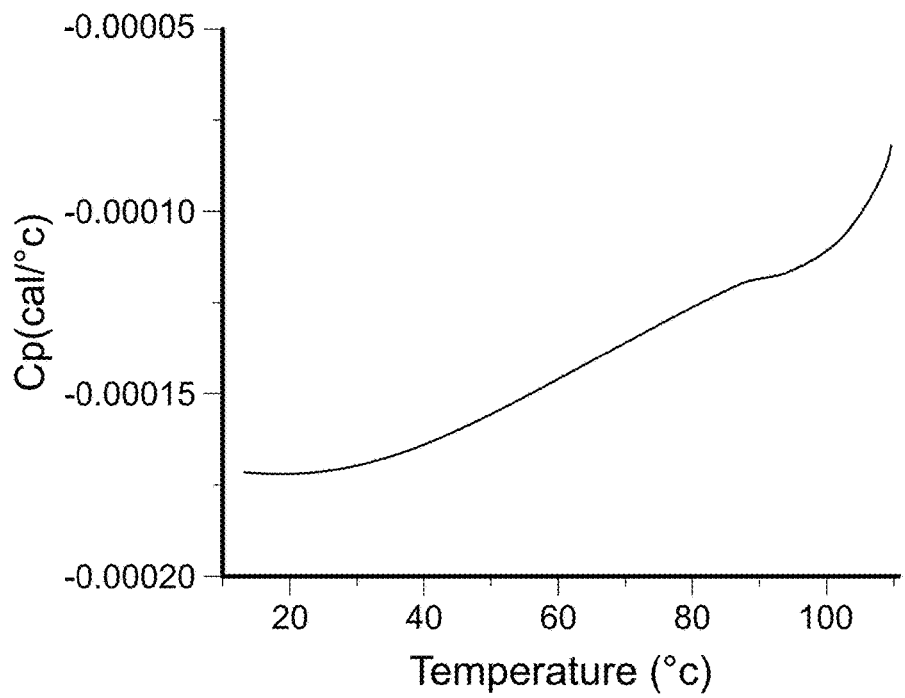
FIG. 1 is a graph depicting results of DSC analysis of sample 75312-F10.

The present invention relates to compositions and methods for treating cancer such as solid tumors, including brain cancers. The compositions include a saposin polypeptide, such as saposin C (SapC), and a phosphatidylserine or structural analog thereof, for example dioleoylphosphatidylserine (DOPS).

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

A "deletion," as the term is used herein, refers to a change in the amino acid or nucleotide sequence that results in the absence of one or more amino acid residues or nucleotides.

The words "insertion" or "addition," as used herein, refer to changes in an amino acid or nucleotide sequence resulting in the addition of one or more amino acid residues or nucleotides, respectively, to the sequence found in the naturally occurring molecule.

The term "fusogenic protein or polypeptide" as used herein refers to a protein or peptide that when added to two separate bilayer membranes can bring about their fusion into a single membrane. The fusogenic protein forces the cell or model membranes into close contact and causes them to fuse. Suitable lysosomal fusogenic proteins and polypeptides for use in this invention include, but are not limited to, proteins of the saposin family.

As used herein, the term "saposin" refers to the family of prosaposin-derived proteins and polypeptides, including but not limited to naturally occurring saposins A, B, C and D (from human or other animal species such as mouse, rat, pig, and cow; see, e.g., Qi et al. (1996) J. Biol. Chem. 271(12): 6874-6880 (incorporated by reference)), as well as synthetic saposin-derived proteins and peptides and peptide analogs showing fusogenic activity. In certain embodiments, the saposin polypeptide comprises or consists of the amino acid sequence of human SapC: Ser Asp Val Tyr Cys Glu Val Cys Glu Phe Leu Val Lys Glu Val Thr Lys Leu Ile Asp Asn Asn Lys Thr Glu Lys Glu Ile Leu Asp Ala Phe Asp Lys Met Cys Ser Lys Leu ProLys Ser Leu Ser Glu Glu Cys Gln Glu Val Val Asp Thr Tyr Gly Ser Ser Ile Leu Ser Ile Leu Leu Glu Glu Val Ser Pro Glu Leu Val Cys Ser Met Leu His Leu Cys Ser Gly (SEQ ID NO:1). In other embodiments, the SapC polypeptide comprises the amino acid sequence of SEQ ID NO:1 with zero to four amino acid insertions, substitutions, or deletions, e.g., a total of one, two, three or four of such changes. In some embodiments, the SapC polypeptide's amino acid sequence comprises SEQ ID NO:1 with one or two amino acid insertions, substitutions, or deletions, or a combination of such changes. Also included are polypeptides analogs possessing some degree of the fusogenic activity of human SapC. By "analog" is meant a polypeptide with substitutions or other alterations in the amino acid sequence of SapC, which substitutions or alterations do not adversely affect the fusogenic properties of the polypeptide. Thus, an analog might be a polypeptide having an amino acid sequence substantially identical to SEQ ID NO:1 and in which one or more amino acid residues have been conservatively substituted with chemically similar amino acids. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. The substitution of a basic residue such as lysine, arginine or histidine for another or the substitution of one acidic residue such as aspartic acid or glutamic acid for another is also contemplated.

SapC and polypeptides derived therefrom may be produced by any useful method, such as, for example, chemically, enzymatically, or recombinantly. Methods for producing polypeptides and fragments thereof are known in the art and include, but are not limited to, chemical peptide synthesis, in vitro translation systems, and expression (and purification from) a recombinant host organism.

"Lipid vesicle" and "liposome" are used interchangeably to refer to a generally spherical cluster or aggregate of amphipathic lipids, typically in the form of one or more concentric layers, for example, bilayers.

The terms "phosphatidylserine" and "phosphatidylserine lipid" are used interchangeably to refer to lipids that have two fatty acids attached in ester linkage to the first and second carbon of glycerol and a serine moiety attached through a phosphodiester linkage to the third carbon of the glycerol. Examples of phosphatidylserine lipids that may be used with the present compositions include but are not limited to the following: dioleoyl phosphatidylserine lipid (DOPS); dihexanoyl phosphatidylserine lipid; dioctanoyl phosphatidylserine lipid; didecanoyl phosphatidylserine lipid; dilauroyl phosphatidylserine lipid; dimyristoyl phosphatidylserine lipid; dipalmitoyl phosphatidylserine lipid; palmitoyl-oleoyl phosphatidylserine lipid; 1-stearoyl-2-oleoyl phosphatidylserine lipid; and diphytanoyl phosphatidylserine lipid, with DOPS being preferred. In aqueous compositions at neutral pH, such phosphatidylserine lipids typically exist in the form of a salt with a cation, and so references to DOPS and other phosphatidylserine lipids used in the present compositions are meant to include both the salt and non-salt forms of the lipids. Suitable cations include any pharmaceutically acceptable cation that forms a salt with the phosphatidylserine lipid, such as any of the following: ammonium ion; L-arginine ion; benzathine ion; deanol ion; diethanolamine (2,2'-iminodiethanol) ion; hydrabamine ion; lysine ion; potassium ion; sodium ion; triethanolamine (2,2', 2"-nitrilotri(ethan-1-ol)) ion; and tromethamine (2-amino-2-(hydroxymethyl)propane-1,3-diol ion. The sodium, potassium, and ammonium salts are preferred.

The compositions of the present invention may contain buffering agents. Exemplary buffering agents include but are not limited to acetate, citrate, histidine, succinate, and tris (hydroxymethyl)aminomethane (Tris; also known as tromethamine), as well as known derivatives of Tris, such as those in which the amino group is modified. In a preferred embodiment, the present aqueous compositions contain Tris at a concentration of 10 to 50 mM (preferably 20 to 30 mM, e.g., 25 mM), and the pH of these compositions ranges from pH 6.8 to 7.6 (e.g., pH 7 to 7.4, e.g., pH 7.1 to 7.3). In some embodiments, the compositions contain citrate buffer or acetate buffer at a concentration of 10 to 50 mM, and the pH of the compositions ranges from pH 5.0 to 8.0.

Biocompatible polymers useful as stabilizing materials and/or bulking agents may be of natural, semi-synthetic (modified natural) or synthetic origin. As used herein, the term polymer denotes a compound comprised of two or more repeating monomeric units, and preferably 10 or more repeating monomeric units. The term semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as inulin), levan, fucoidan, carrageenan, galatocarolose, pectic acid, pectin, amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch, and various other natural homopolymers or heteropolymers, such as those containing one or more of the following aldoses, ketoses, acids or amines: erythrose, threose, ribose, arabinose, xylose, lyxose, allose, altrose, lucose, mannose, gulose, idose, galactose, talose, erytirulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol (PEG), polyoxyethylene, and polyethylene terephthalate), polypropylenes (such as, for example, polypropylene glycol), polyurethanes (such as, for example, polyvinyl alcohol (PVA), polyvinyl chloride and polyvinylpyrrolidone (PVP)), polyamides including nylon, polystyrene, polylactic acids, fluorinated hydrocarbons, fluorinated carbons (such as polytetrafluoroethylene), and polymethylmethacrylate, and derivatives of any of these. Methods for the preparation of vesicle compositions that employ polymers as stabilizing compounds will be readily apparent to those skilled in the art, once armed with the present disclosure, when the present disclosure is coupled with information known in the art, such as that described and referred to in U.S. Pat. No. 5,205,290, the disclosures of which are hereby incorporated herein by reference in their entirety. In preferred form, the present compositions contain one or more of mannitol, lactose, trehalose, sucrose, PEG, PVP, sorbitol, or glucose.

A wide variety of techniques are available for the preparation of the claimed compositions. In a preferred embodiment, DOPS or another phosphatidylserine lipid is solubilized with organic solvent and then combined with the aqueous-based ingredients, including SapC, at ambient temperature for 5-15 minutes. Exemplary organic solvents that may be used for this purpose include but are not limited to ethanol, DMSO, n-butanol, and t-butanol (also known as t-butyl alcohol, TBA). In a preferred embodiment, the organic solvent is t-butanol, e.g., at over 98% purity. When the ingredients are mixed, the lipid and SapC together form into vesicles suspended in the aqueous solution. Lyophilization of the mixture drives off not only the water, but also most or all of the organic solvent. In preferred embodiments, the lyophilized powder contains less than 3% w/w TBA.

A wide variety of techniques known to those of ordinary skill in the art can be used to prepare liposome compositions. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, controlled detergent dialysis, and others. See, e.g., Madden et al., Chemistry and Physics of Lipids, 1990 53, 37-46, the disclosures of which are hereby incorporated herein by reference in their entirety. Suitable freeze-thaw techniques are described, for example, in International Application Ser. No. PCT/US89/05040, filed Nov. 8, 1989, the disclosures of which are incorporated herein by reference in their entirety. Preparation of the liposomes may be carried out in a solution, such as an aqueous saline solution, aqueous phosphate buffer solution, or sterile water. The liposomes may be prepared by various processes that involve shaking or vortexing.

Many liposomal preparatory techniques that may be adapted for use in the preparation of vesicle compositions are discussed, for example, in U.S. Pat. No. 4,728,578; U.K. Patent Application GB 2193095 A; U.S. Pat. Nos. 4,728, 575; 4,737,323; International Application Ser. No. PCT/US85/01161; Mayer et al., Biochimica et Biophysica Acta, Vol. 858, pp. 161-168 (1986); Hope et al., Biochimica et Biophysica Acta, Vol. 812, pp. 55-65 (1985); Mayhew et al., Methods in Enzymology, Vol. 149, pp. 64-77 (1987); Mayhew et al., Biochimica et Biophysica Acta, Vol 755, pp. 169-74 (1984); Cheng et al, Investigative Radiology, Vol. 22, pp. 47-55 (1987); International Application Ser. No. PCT/US89/05040; U.S. Pat. Nos. 4,533,254; 4,162,282; 4,310,505; 4,921,706; and Liposome Technology, Gregoriadis, G., ed., Vol. 1, pp. 29-31, 51-67 and 79-108 (CRC Press Inc., Boca Raton, Fla. 1984), the disclosures of each of which are hereby incorporated by reference in their entirety.

As those skilled in the art will recognize, any of the vesicle compositions may be lyophilized for storage and reconstituted, for example, with a sterile aqueous medium suitable for administration to a patient (such as water, phosphate buffered solution, Tris buffered solution, or aqueous saline solution), if necessary with the aid of vigorous agitation. The liposomes may be lyophilized according to methods known in the art, including those described in Rey, L. (2010), Freeze-Drying/Lyophilization of Pharmaceutical and Biological Products. ISBN 9781439825754, the relevant parts of which are incorporated by reference. Exemplary lyophilization methods utilize freezing, primary drying, and secondary drying phases according to parameters disclosed in Table I.

TABLE I

Exemplary ranges of lyophilization parameters

| Cycle Step | Temperature, ° C. | Pressure, mTorr | Duration, minutes |
| --- | --- | --- | --- |
| Freezing | −40 to −50 (no higher than −40) | — | 340-960 |
| Primary Drying | −15 to −25 | 30-65 | 2200-4300 |
| Secondary Drying | 25 to 35 | 35-65 | 500-2300 |
| Total Cycle | — | — | 3040-7560 |

To prevent agglutination or fusion of the lipids and/or vesicles as a result of lyophilization, it may be useful to include additives that prevent such fusion or agglutination from occurring. Additives that may be useful include sorbitol, mannitol, sodium chloride, glucose, trehalose, polyvinylpyrrolidone (PVP) and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety.

The terms "stable" and "stabilized", as applied to vesicles, mean that the vesicles are substantially resistant to degradation, including, for example, loss of vesicle structure or encapsulated gas or gaseous precursor, for a useful period of time. The terms "stable" and "stabilized" as applied to the present aqueous compositions containing SapC/lipid vesicles (before lyophilization or after reconstitution of the lyophilized powder) mean that there is no significant loss of content or purity of protein or of phosphatidylserine lipid and no significant changes in the physical properties. The terms "stable" and "stabilized" as applied to the present lyophilized powder compositions mean that, upon reconstitution with water for injection, there is no significant loss on content or purity of protein and phosphatidylserine lipid and no significant changes on the physical properties.

Cancers that are treatable with the present compositions include, for example, any solid tumors or neurological cancer, e.g., prostate cancer, liver cancer, lung cancer, pancreatic cancer, renal cell carcinoma, breast cancer, ovarian cancer, testicular cancer, ependymoma, brain cancers such as high grade gliomas (HGG) including glioblastoma multiforme (GBM), and gastrointestinal (GI) cancers including appendiceal and colorectal. The compositions are useful for treating metastatic tumors regardless of the primary tumor type or the organ where it metastasizes. A metastatic tumor can arise from a multitude of primary tumor types, including but not limited to those of prostate, colon, lung, breast, and liver origin. The terms "cancer" and "neoplasm" can include malignancies of the various organ systems, such as those affecting the lung, breast, thyroid, lymphoid, gastrointestinal, or genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. Further details can be found in, for example, U.S. Pat. No. 7,834,147, which is incorporated herein by reference in its entirety.

"Patient" or "subject" refers to an animal, including a mammal, preferably a human.

A therapeutically effective dose or amount of the composition is an amount useful to treat a patient's cancer. In general, a single therapeutically effective dose of the present composition will contain an amount of SapC (or its derivative) in the range of about 0.01 to 30 mg/kg body weight, preferably about 0.05 to 20 mg/kg body weight, more preferably about 0.1 to 15 mg/kg body weight, and even more preferably about 0.5 to 10 mg/kg. For example, the amount of SapC in a single intravenous dose can be about 0.7 mg/kg, 1.1 mg/kg, 1.4 mg/kg, 1.8 mg/kg, 2.4 mg/kg, 2.8 mg/kg, 3.0 mg/kg, 3.2 mg/kg, 3.6 mg/kg, or more. A given patient may receive a given dose level for one or more initial administrations and a different (lower or higher) level for further administrations. The delivery may be by any suitable injectable route, e.g., intravenous, intra-arterial, intradermal, intramuscular, intracardiac, intracranial, subcutaneous, or intraperitoneal. Typically, the composition of the invention is reconstituted in sterile water for injection and is delivered by intravenous infusion in an IV bag containing an isotonic carrier, such as saline, PBS, or dextrose 5% by weight (D5W). Further details regarding routes of administration can be found, for example, in U.S. Pat. No. 7,834,147.

Administration can occur at least once a day for some number of consecutive days, e.g., for 3, 4, 5, 6, 7, 8, 9, or more consecutive days, or can be, e.g., every other day, or 3 times a week, or once every 7±3 days, or once every 14±3 days, or once every 28±3 days. The timing of administrations can start with one of those schedules and after a suitable period of treatment change to another that is more or less frequent. The entire period of treatment can be completed in, e.g., eight or twelve or sixteen weeks, or up to six months, but more preferably will continue as long as the patient appears to be benefiting from the treatment. For example, the dosing schedule might be:

Cycle 1:
 week 1: one dose on each of days 1-5;
 week 2: 3x/week every other day, e.g. one dose on each of days 8, 10, and 12;
 weeks 3 and 4: one dose each week (every 7 (+/−3) days);
Cycle 2: one dose during week 5;
and any subsequent cycle: one dose 28 (+/−3) days after the most recent prior dose.

The molar ratio of the SapC polypeptide to the phosphatidylserine lipid in a composition of the invention can be in the range from 1:2 to 1:50, for example 1:5 to 1:30, or 1:8 to 1:20, or 1:11 to 1:13. Suitable molar ratios include but are not limited to 1:10, 1:11, 1:12, 1:13, 1:14, and 1:15. The mass ratio of the polypeptide to the phosphatidylserine lipid is in the range from about 1:0.18 to about 1:4.5, or about 1:0.45 to about 1:2.7, or about 1:0.72 to about 1:1.81, or about 1:1 to about 1:1.2. It is recognized that the preferred ratio of the polypeptide and lipid in a composition of the invention may be affected by certain factors such as, but not limited to, the target cell type and the route of delivery.

Useful background information and technical details can be found in U.S. Pat. Nos. 7,834,147 and 9,271,932, which are incorporated herein by reference in their entirety.

The compositions and methods are further supported by the information provided in the following Examples. It is to be understood that the embodiments described in the Examples are merely illustrative, and are not intended to limit the scope of the present invention, which will be limited only by the appended claims.

EXAMPLES

Materials

The following reagents were purchased from commercial vendors: sodium citrate dihydrate, citric acid anhydrous, glycine, sodium phosphate monobasic monohydrate (EMD), sodium phosphate dibasic heptahydrate (Thermo Scientific), tris(hydroxymethyl)aminomethane ("Tris;" J. T. Baker), L-histidine, sodium chloride, HyClone™ water (Thermo Scientific), sodium hydroxide, D-trehalose anhydrous (VWR International), D(+) trehalose dihydrate (Spectrum), sucrose (BDH Chemicals), mannitol (BDH Chemicals), 0.9% sodium chloride, t-butanol (Sigma Aldrich), 1,2-dioleoyl-sn-glycero-3-phospho-L-serine (DOPS sodium salt) (Avanti Polar Lipids).

Saposin C ("SapC") was prepared by standard methods utilizing recombinant expression in *E. coli* cells.

Example 1. Determination of how Select Buffering Agents Affect Stability of Compositions Comprising SapC To determine how buffering agents affect SapC stability, compositions of SapC in select buffering agents listed in Tables 1 and 2 were prepared and analyzed by differential scanning calorimetry (DSC) and circular dichroism (CD).

Methods

The compositions listed in Table 1 and Table 2 were prepared.

TABLE 1

Compositions prepared for DSC analysis

| UID | Description |
|---|---|
| 75312-F9 | 5 mg/mL SapC, 10 mM citrate pH 6 |
| 75312-F10 | 5 mg/mL SapC, 10 mM phosphate pH 7 |
| 75312-F11 | 5 mg/mL SapC, 10 mM Tris pH 7.5 |
| 75312-F12 | 5 mg/mL SapC, 10 mM Tris pH 8 |
| 75312-F13 | 5 mg/mL SapC, 10 mM phosphate pH 7.5, 1.68% w/v NaCl |
| 75312-F14 | 5 mg/mL SapC, 50 mM phosphate pH 7.5, 1.20% w/v NaCl |
| 75312-F15 | 5 mg/mL SapC, 10 mM glycine pH 9 |

TABLE 2

Compositions prepared for CD analysis

| UID | Description |
|---|---|
| 75312-F1 | 1 mg/mL SapC, 10 mM citrate pH 6 |
| 75312-F2 | 1 mg/mL SapC, 10 mM phosphate pH 7 |
| 75312-F3 | 1 mg/mL SapC, 10 mM Tris pH 7.5 |
| 75312-F4 | 1 mg/mL SapC, 10 mM Tris pH 8 |
| 75312-F5 | 1 mg/mL SapC, 10 mM phosphate, 1.68% w/v NaCl, pH 7.5 |
| 75312-F6 | 1 mg/mL SapC, 50 mM phosphate, 1.20% w/v NaCl, pH 7.5 |
| 75312-F7 | 1 mg/mL SapC, 10 mM glycine pH 9 |

DSC measurements were performed using a MicroCal™ VP-DSC calorimeter (Northampton, Mass.). Run parameters included a temperature range of 10 to 110° C., scan rate of 60° C. per hour, and filtering period of 16 seconds. The samples were pre-equilibrated for 15 minutes prior to each scan. The thermograms were processed using the MicroCal™ VP-DSC calorimeter add-on module for Origin version 7. A DSC melt detects the unfolding of a protein by monitoring the change in enthalpy associated with the event. Protein unfolding is commonly exothermic and is marked by a peak in the thermogram reading, with the apex depicting the transition at which half of the protein molecules are unfolded. A high melting temperature (Tm) signifies a high intrinsic conformational stability.

CD measurements were performed using a Chirascan™-plus spectropolarimeter (Leatherhead, UK) with a 4-position peltier temperature controller. A far-UV spectrum of each sample was obtained over a wavelength range of 180-260 nm at 10° C. using a 0.1 cm path length cuvette. The spectra of respective control samples were subtracted from the spectra for corresponding test samples. The percent of secondary structure was estimated using CDNN software provided with the instrument. It was determined that samples with 1 mg/mL SapC concentration needed to be diluted to avoid saturation at the lower wavelengths of the CD spectra. Therefore, a 6-fold dilution was performed for each of the samples prior to CD measurements.

Results

FIG. 1 is a graph depicting results of DSC analysis of sample 75312-F10. The thermogram for sample 75312-F10, and also for all samples tested (data not shown), lacked a transition expected for protein unfolding. Without wishing to be bound to a particular theory, applicants hypothesize that either (1) the SapC protein lacks tertiary structure(s) or (2) the SapC protein does not unfold even up to the highest temperature of 110° C.

Figure 2:
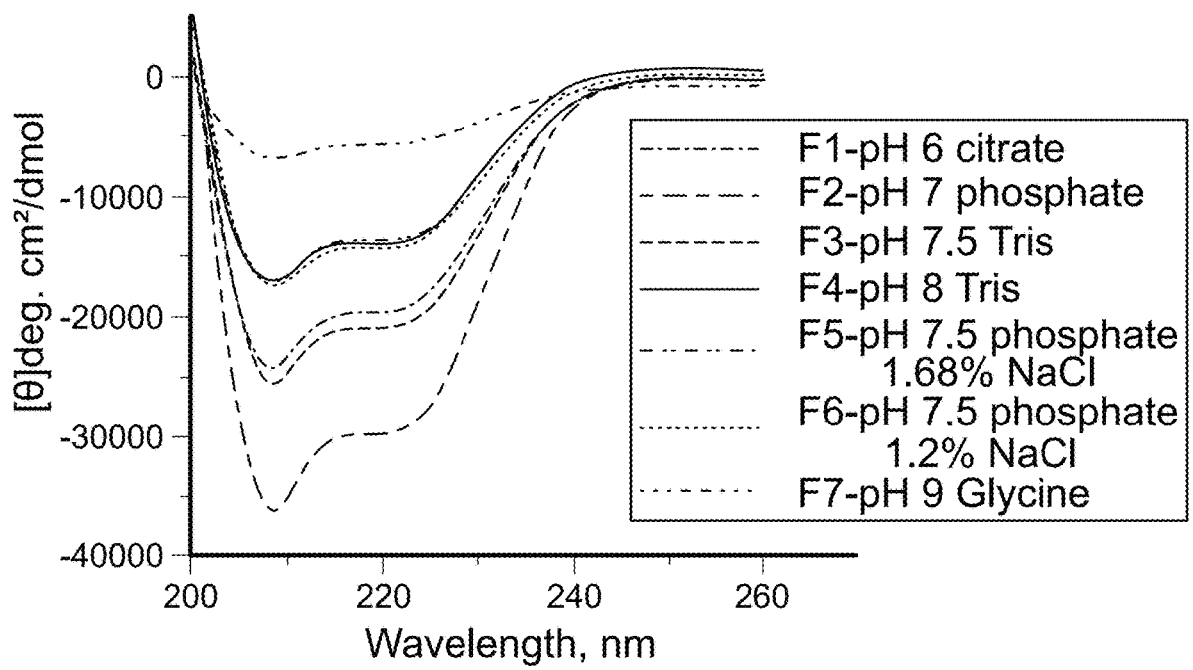
FIG. 2 is a graph depicting results of CD analysis of samples listed in Table 2.

FIG. 2 is a graph depicting results of CD analysis of samples listed in Table 2. The CD spectra of all samples exhibit minima at approximately 208 and 220 nm, a characteristic indicative of significant α-helix content. Analysis of the spectra revealed a pH-dependence in the magnitudes of the spectra in order of pH 7.0>7.5≈6.0>8.0>9.0.

Figure 3:
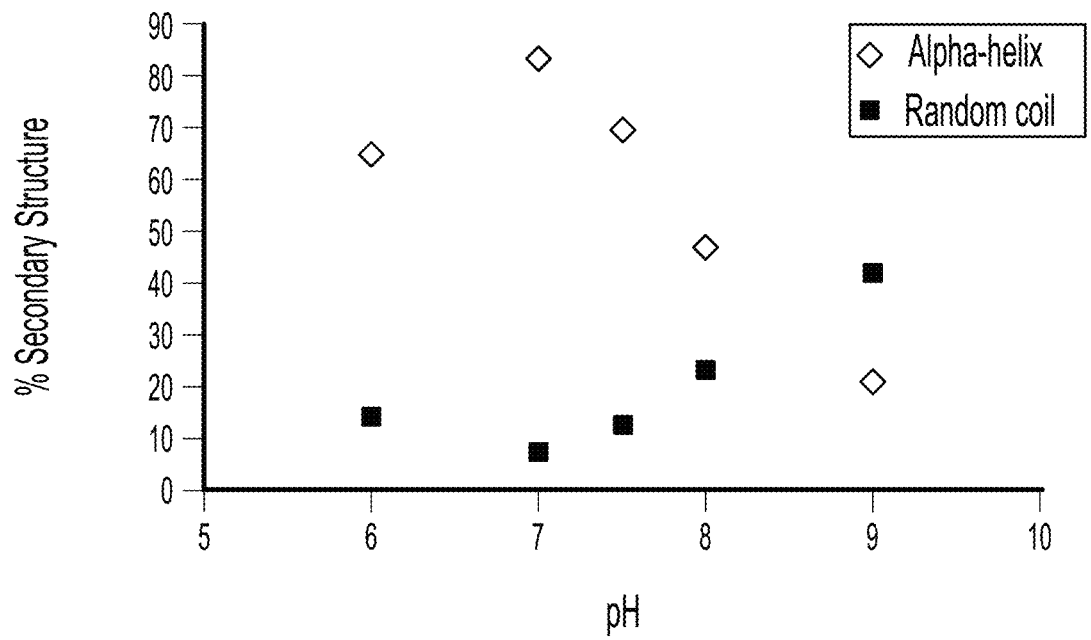
FIG. 3 is a graph depicting the percentage of α-helix and random coil as estimated from CD analysis of samples listed in Table 2.

The percent of secondary structure for each sample was estimated from the CD spectra using methods known in the art and is reported in Table 3. FIG. 3 is a graph depicting the percentage of α-helix and random coil as estimated from CD analysis of samples listed in Table 2. Notably, the highest and lowest amounts of α-helix correlated with sample pH, with highest amount in 75312-F2 (pH 7) and the lowest in 75312-F7 (pH 9). These data indicate that SapC likely retains activity, as inferred from the preservation of secondary structure components, when stored in phosphate at pH 7 or in Tris pH 7.6 These data also indicate that varying buffer concentration, specifically 10 or 50 mM phosphate (comparison of 75312-F5 to 75312-F6), while holding tonicity constant did not confer differences in secondary structure of SapC.

TABLE 3

Estimated percent secondary structure in each composition

| UID | Helix | Anti-parallel β-sheet | Parallel β-sheet | β-turn | Random coil | Total sum |
|---|---|---|---|---|---|---|
| 75312-F1 | 64.9 | 3.2 | 3.3 | 12.5 | 14.0 | 97.9 |
| 75312-F2 | 83.4 | 1.4 | 1.6 | 9.7 | 7.2 | 103.4 |
| 75312-F3 | 69.6 | 2.7 | 2.8 | 11.8 | 12.5 | 99.4 |
| 75312-F4 | 46.6 | 5.7 | 5.8 | 14.9 | 23.1 | 96.2 |
| 75312-F5 | 45.4 | 6.0 | 6.0 | 15.1 | 23.5 | 96.0 |
| 75312-F6 | 47.0 | 5.7 | 5.7 | 14.9 | 22.8 | 96.1 |
| 75312-F7 | 21.0 | 13.6 | 13.0 | 19.6 | 42.1 | 109.4 |

Example 2. Determination of how Select Buffering Agents (and Concentrations) Affect Stability and Purity of SapC Compositions Stored at 60° C.

To determine how various buffering agents affect stability and purity of compositions comprising SapC, compositions of SapC in select buffering agents listed in Table 4 were prepared, stored at 60° C., and analyzed by visual appearance, total protein content, and purity of protein content.

Methods

The compositions listed in Table 4 were prepared. Some samples were frozen immediately upon preparation (t=0 days) and held at −70° C. until time for analysis; others were stored for 10 days at 60° C. (t=10 days) before being frozen and held at −70° C. until time for analysis. The frozen samples were then thawed to room temperature and the following properties were assayed: (1) appearance assessed by visual characterization of liquid under bright light to observe clarity, color, and presence of any particulate matter in the sample; (2) pH quantified by pH meter; (3) total protein content quantified by UV analysis at 280 nm using an extinction coefficient of 0.395 $mg^{-1}$ mL $cm^{-1}$; (4) purity of protein content, specifically the percentage of full length SapC in the sample and the presence of (and concentration of) SapC degradation products as assessed by SE-HPLC, RP-HPLC, and IEX-HPLC. SE-HPLC, RP-HPLC, and IEX-HPLC are chromatography methods that separate the analyte by size, by hydrophobicity, and by charge variants, respectively.

TABLE 4

List of compositions

| UID | Description |
|---|---|
| 183-001-01-095-F1 | 2 mg/mL SapC, 10 mM histidine pH 6 |
| 183-001-01-095-F2 | 2 mg/mL SapC, 50 mM histidine pH 6 |
| 183-001-01-095-F3 | 5 mg/mL SapC, 10 mM histidine pH 6 |
| 183-001-01-095-F4 | 5 mg/mL SapC, 50 mM histidine pH 6 |
| 183-001-01-095-F5 | 2 mg/mL SapC, 10 mM phosphate pH 6.8 |
| 183-001-01-095-F6 | 2 mg/mL SapC, 50 mM phosphate pH 6.8 |
| 183-001-01-095-F7 | 5 mg/mL SapC, 10 mM phosphate pH 6.8 |
| 183-001-01-095-F8 | 5 mg/mL SapC, 50 mM phosphate pH 6.8 |
| 183-001-01-095-F9 | 2 mg/mL SapC, 10 mM Tris pH 7.6 |
| 183-001-01-095-F10 | 2 mg/mL SapC, 50 mM Tris pH 7.6 |
| 183-001-01-095-F11 | 5 mg/mL SapC, 10 mM Tris pH 7.6 |
| 183-001-01-095-F12 | 5 mg/mL SapC, 50 mM Tris pH 7.6 |

Results

The visual appearances of the samples are summarized in Table 5. At t=0 days, 183-001-01-095-F2, -F4, -F5, -F6, and -F7 were free of visible particles, while 183-001-01-095-F1, -F3, -F8, -F9, -F10, -F11, and -F12 were mostly clear with a few particles. After incubation at 60° C. for 10 days, all samples had a few particles, with phosphate-buffered 183-001-01-095-F5, -F6, and -F8 having "long" particles. Additionally, some histidine and phosphate-containing samples took on a slight yellow tint, specifically 183-001-01-095-F3, -F4, -F7, and -F8.

TABLE 5

Appearance of each composition after t = 0 and t = 10 days

| UID | t = 0 days | t = 10 days |
|---|---|---|
| 183-001-01-095-F1 | Clear, colorless, few particles | Clear, colorless, few particles |
| 183-001-01-095-F2 | Clear, colorless, free of visible particles | Clear, slight yellow tint, few particles |
| 183-001-01-095-F3 | Clear, colorless, few particles | Clear, slight yellow tint, few particles |
| 183-001-01-095-F4 | Clear, colorless, free of visible particles | Clear, slight yellow tint, few particles |
| 183-001-01-095-F5 | Clear, colorless, free of visible particles | Clear, colorless, few long particles |
| 183-001-01-095-F6 | Clear, colorless, free of visible particles | Clear, colorless, few long particles |
| 183-001-01-095-F7 | Clear, colorless, free of visible particles | Clear, slight yellow tint, few particles |
| 183-001-01-095-F8 | Clear, colorless, few particles | Clear, slight yellow tint, few long particles |
| 183-001-01-095-F9 | Clear, colorless, few particles | Clear, colorless, few particles |
| 183-001-01-095-F10 | Clear, colorless, few particles | Clear, colorless, few particles |
| 183-001-01-095-F11 | Clear, colorless, few particles | Clear, colorless, few particles |
| 183-001-01-095-F12 | Clear, colorless, few particles | Clear, colorless, few particles |

The pH of each sample is reported in Table 6. The samples buffered by phosphate (183-001-01-095-F5, -F6, -F7, -F8) drifted to a more basic pH than their target pH of 6.8, at both time points. Notably, the pH of samples buffered by 10 mM phosphate (183-001-01-095-F5 and -F7) drifted more than the samples buffered with 50 mM phosphate (183-001-01-095-F6 and -F8). All the samples buffered with histidine (183-001-01-095-F1, -F2, -F3, and -F4) or Tris (183-001-01-095-F9, -F10, -F11, and -F12) maintained their initial pH value to within 0.1 pH units.

TABLE 6 pH of each sample after t = 0 and t = 10 days

| UID | t = 0 days | t = 10 days |
|---|---|---|
| 183-001-01-095-F1 | 6.12 | 6.11 |
| 183-001-01-095-F2 | 5.98 | 5.96 |
| 183-001-01-095-F3 | 6.22 | 6.25 |
| 183-001-01-095-F4 | 6.01 | 6.01 |
| 183-001-01-095-F5 | 7.31 | 7.29 |
| 183-001-01-095-F6 | 7.10 | 7.09 |
| 183-001-01-095-F7 | 7.25 | 7.30 |
| 183-001-01-095-F8 | 7.08 | 7.09 |
| 183-001-01-095-F9 | 7.55 | 7.57 |
| 183-001-01-095-F10 | 7.54 | 7.54 |
| 183-001-01-095-F11 | 7.59 | 7.60 |
| 183-001-01-095-F12 | 7.52 | 7.53 |

Figure 4:
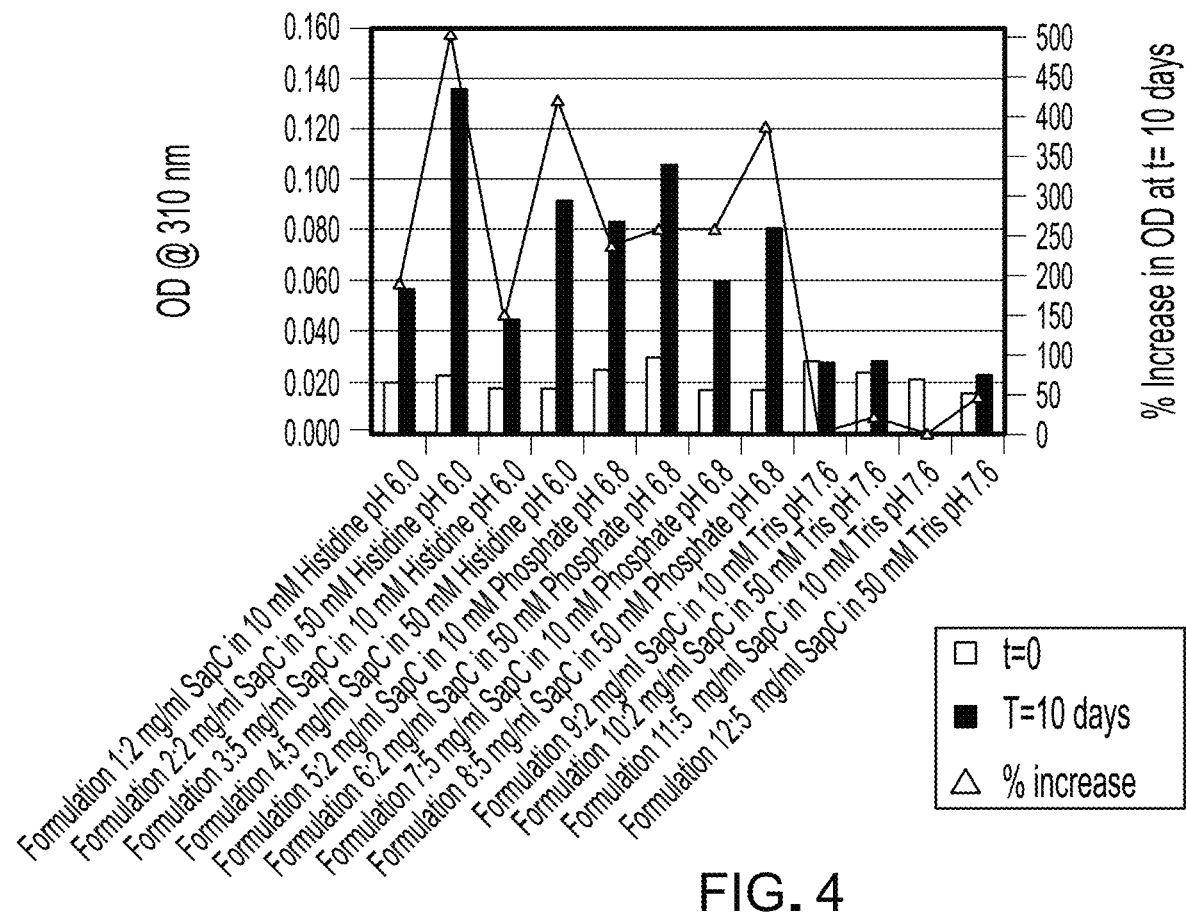
FIG. 4 is a graph depicting, for each sample listed in Table 4, the optical density value at 310 nm.

The total protein content in each of the samples is reported in Table 7. At t=0, all samples exhibited protein concentrations that were close to the target values of either 2 or 5 mg/mL. At t=10 days, however, a majority of the samples had increased protein concentration. These inflated numbers are probably an artifact of spectral scattering due to the increase in large particles in the samples. To quantify the increase in scattering, optical density scans (200 to 400 nm) were measured for each sample to evaluate the extent of scattering increase upon storage. FIG. 4 is a graph depicting for each sample the optical density value at 310 nm, a wavelength devoid of significant absorption signal (note that sample 183-001-01-095-F11 was not analyzed). The samples buffered by histidine at pH 6 (183-001-01-095-F1, -F2, -F3, and -F4) and samples buffered by phosphate at pH 6.8 (183-001-01-095-F5, -F6, -F7, and -F8) exhibited increased scattering after 10 days. Notably, the samples 183-001-01-095-F9, -F10, and -F12 buffered by Tris at pH 7.6 exhibited minimal increases in scattering after 10 days.

TABLE 7

Total protein content (mg/mL) in compositions after t = 0 and t = 10 days

| UID | t = 0 days | t = 10 days |
|---|---|---|
| 183-001-01-095-F1 | 2.01 | 2.34 |
| 183-001-01-095-F2 | 2.08 | 3.12 |
| 183-001-01-095-F3 | 4.82 | 5.57 |
| 183-001-01-095-F4 | 4.97 | 6.70 |
| 183-001-01-095-F5 | 2.08 | 2.36 |
| 183-001-01-095-F6 | 2.13 | 2.52 |
| 183-001-01-095-F7 | 4.99 | 5.53 |
| 183-001-01-095-F8 | 5.00 | 5.92 |
| 183-001-01-095-F9 | 2.07 | 2.09 |
| 183-001-01-095-F10 | 2.03 | 2.09 |
| 183-001-01-095-F11 | 5.05 | 5.18 |
| 183-001-01-095-F12 | 4.99 | 5.22 |

Figure 5:
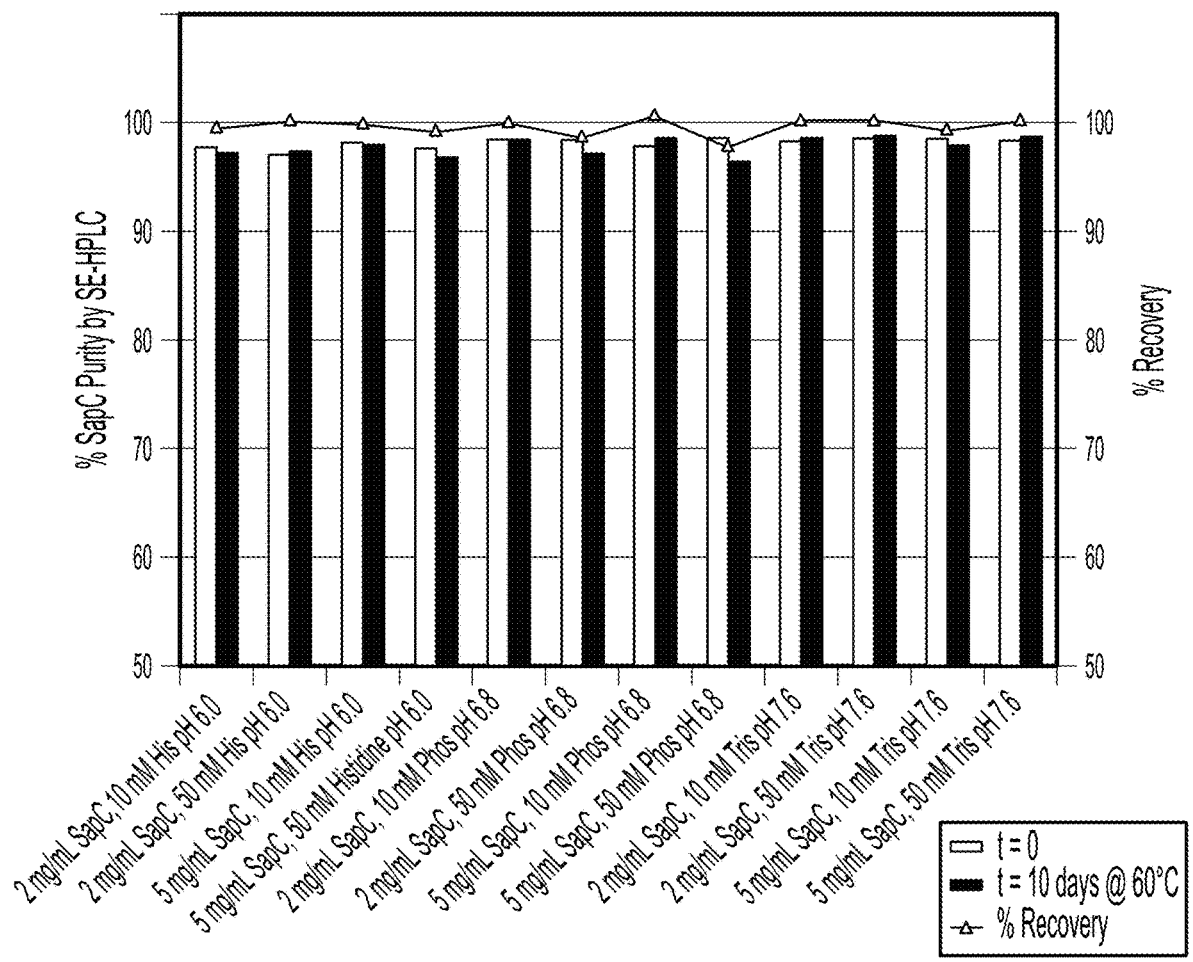
FIG. 5 is a graph depicting SE-HPLC measurements of SapC purity at t=0 and after 10 days at 60° C. for samples listed in Table 4.

The purity of SapC in the samples was estimated by SE-HPLC, RP-HPLC, and IEX-HPLC. The purity of SapC in the samples was quantified as the percentage of protein content detected in elution peak comprising full length SapC. FIG. 5 is a graph depicting SE-HPLC measurements of SapC purity at t=0 and after 10 days at 60° C. All samples exhibited greater than 95 percent purity of SapC after 10 days, as detected by SE-HPLC. Notably, the samples buffered by histidine at pH 6 (183-001-01-095-F1, -F2, -F3, and -F4) and samples buffered by phosphate at pH 6.8 (183-001-01-095-F5, -F6, -F7, and -F8) that exhibited increased scattering at OD 310 nm were expected to contain higher order molecular weight species (i.e., aggregates); however, no such species were observed by SE-HPLC in these samples. If these supposed aggregates were too large to pass through the column, then the apparent concentration of the protein (based on chromatographic area) would have decreased. This, too, was not observed, as SapC main peak recovery was high even after 10 days in those samples. Without wishing to be bound to a particular theory, applicants note a possibility that could explain these results is that the particulate matter observed in F1-F8 does not comprise, or comprises a negligible amount of, SapC or fragments of SapC.

Figure 6:
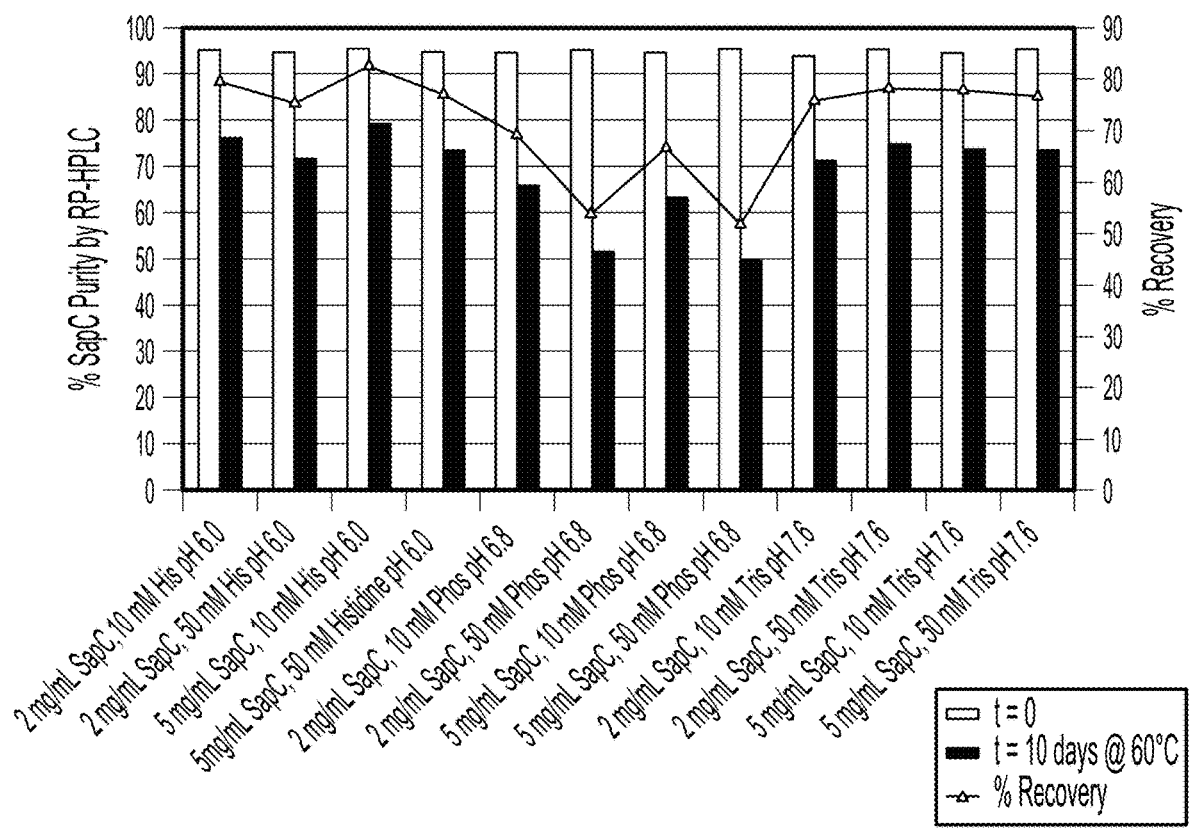
FIG. 6 is a graph depicting RP-HPLC measurements of SapC purity at t=0 and after 10 days at 60° C. for samples listed in Table 4.

FIG. 6 is a graph depicting RP-HPLC measurements of SapC purity at t=0 and after 10 days at 60° C. All samples exhibited some degree of decreased SapC purity after 10 days, as measured by RP-HPLC. The samples buffered by phosphate pH 6.8 (183-001-01-095-F5, -F6, -F7, and -F8) exhibited the largest decreases in SapC purity.

Figure 7:
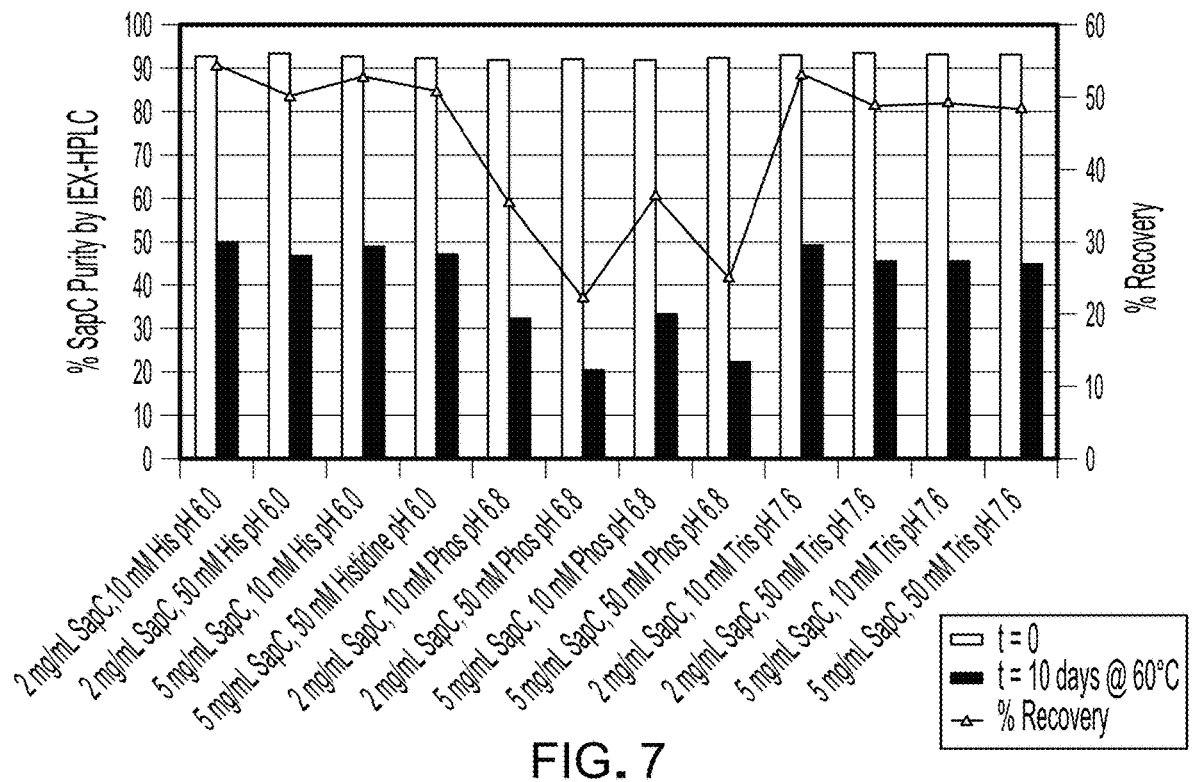
FIG. 7 is a graph depicting IEX-HPLC measurements of SapC purity at t=0 and after 10 days at 60° C. for samples listed in Table 4.

FIG. 7 is a graph depicting IEX-HPLC measurements of SapC purity at t=0 and after 10 days at 60° C. All samples exhibited some degree of decreased SapC purity after 10 days, as measured by IEX-HPLC. As was true when the measurements were done with RP-HPLC (see above), the samples buffered by phosphate pH 6.8 (183-001-01-095-F5, -F6, -F7, and -F8) exhibited the largest decreases in SapC purity.

In sum, these data indicate that samples comprising Tris at pH 7.6 exhibited higher stability and purity compared to samples comprising histidine at pH 6 or phosphate at pH 6.8.

Example 3. Determination of how Select Concentrations of Citrate at pH 6.2 Affects Stability and Purity of Compositions Comprising SapC Exposed to 60° C.

To determine how citrate affects the stability and purity of compositions comprising SapC, various compositions of SapC in citrate at pH 6.2 were prepared, stored at 60° C., and analyzed by appearance, pH, protein content, and chromatography methods.

Methods

Samples of the compositions listed in Table 8 were taken at t=0 (immediately upon preparation) and after storage at 60° C. for 10 days (t=10 days), then frozen and stored at −70° C. until time for analysis. The frozen compositions were thawed to room temperature, and the following properties were assayed as described in Example 2: visual appearance, pH, total protein content, and purity of protein content.

TABLE 8

Citrate-containing compositions

| UID | Description |
|---|---|
| 82014-F1 | 2 mg/mL SapC, 10 mM citrate pH 6.2 |
| 82014-F2 | 2 mg/mL SapC, 50 mM citrate pH 6.2 |
| 82014-F3 | 5 mg/mL SapC, 10 mM citrate pH 6.2 |
| 82014-F4 | 5 mg/mL SapC, 50 mM citrate pH 6.2 |
| 82014-citrate control 1 | 10 mM citrate pH 6.2 |
| 82014-citrate control 2 | 50 mM citrate pH 6.2 |

Results

The visual appearance and pH of each sample are reported in Table 9. All of the samples were clear and colorless liquids at both time points. The pH of all samples was maintained within 0.2 pH units of the initial pH value after 10 days at 60° C.; however, the initial pH of all samples was more basic than the targeted pH 6.2.

TABLE 9

Visual appearance and pH for each sample after t = 0 and t = 10 days

| Sample # | Time Point | Appearance | pH |
|---|---|---|---|
| 82014-F1 | t = 0 | Clear, colorless solution | 6.62 |
|  | t = 10 | Clear, colorless solution | 6.63 |
| 82014-F2 | t = 0 | Clear, colorless solution | 6.32 |
|  | t = 10 | Clear, colorless solution | 6.26 |
| 82014-F3 | t = 0 | Clear, colorless solution | 6.71 |
|  | t = 10 | Clear, colorless solution | 6.92 |
| 82014-F4 | t = 0 | Clear, colorless solution | 6.31 |
|  | t = 10 | Clear, colorless solution | 6.32 |
| 82014-Citrate Control 1 | t = 0 | Clear, colorless solution | 6.48 |
|  | t = 10 | Clear, colorless solution | 6.64 |
| 82014-Citrate Control 2 | t = 0 | Clear, colorless solution | 6.29 |
|  | t = 10 | Clear, colorless solution | 6.31 |

Figure 8:
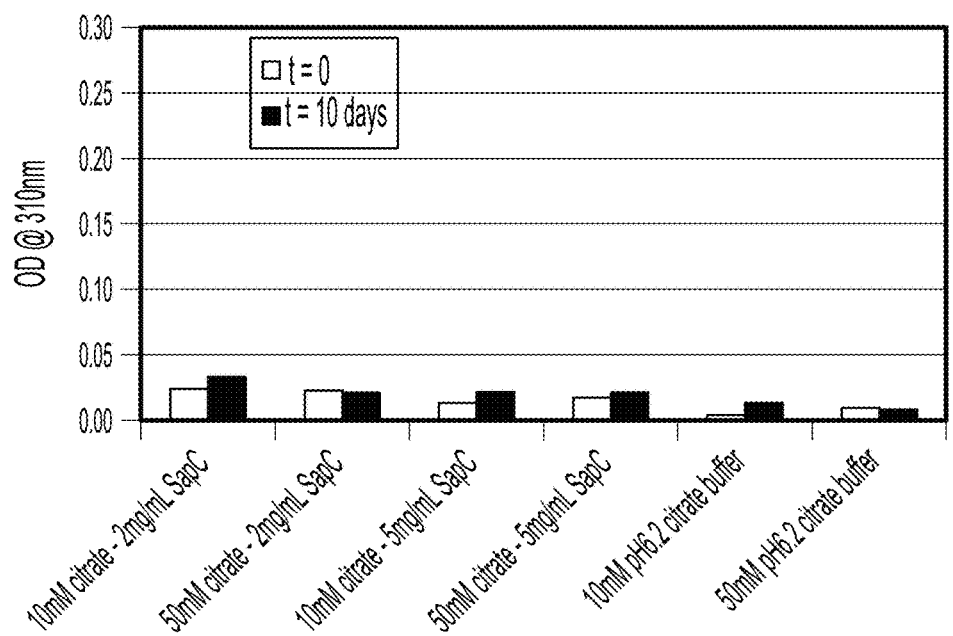
FIG. 8 is a graph depicting optical density when assayed at 310 nm for each Table 8 composition at t=0 and after 10 days at 60° C.

FIG. 8 is a graph depicting optical density when assayed at 310 nm for each Table 8 composition at t=0 and after 10 days at 60° C. No composition exhibited a significant increase in optical density at 310 nm after 10 days.

Figure 9:
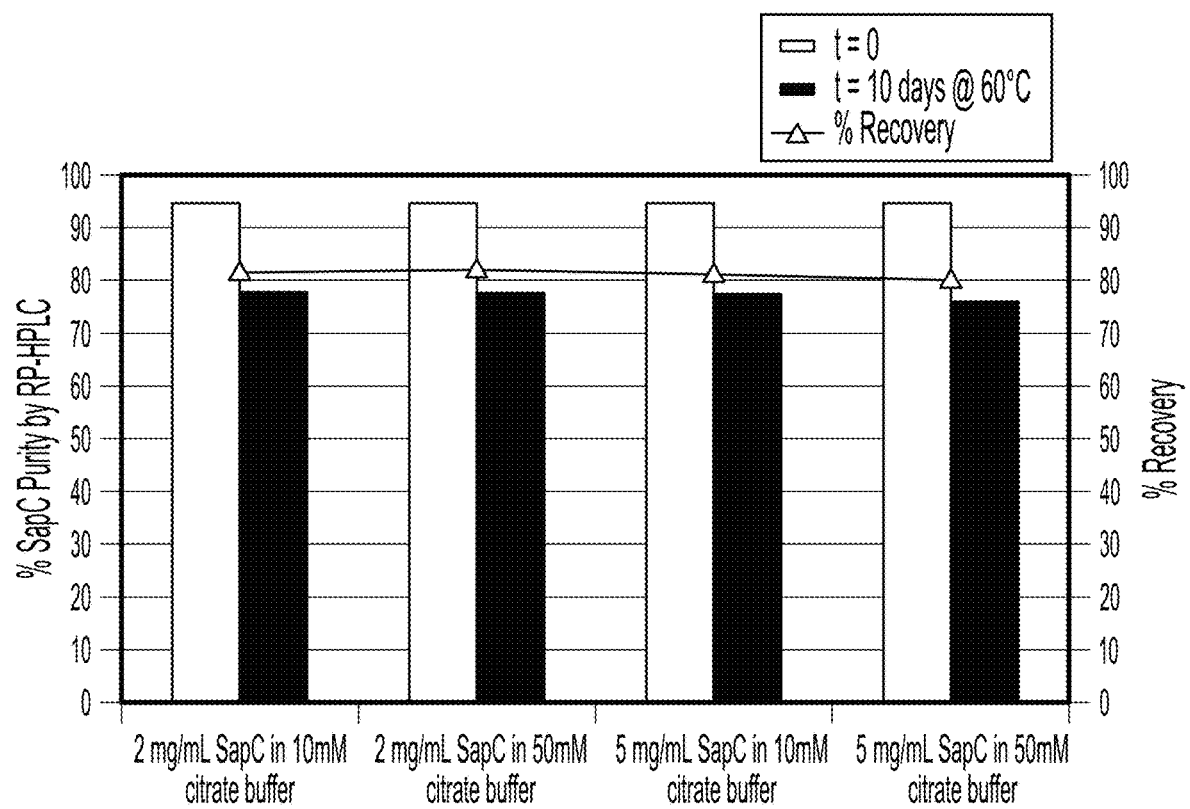
FIG. 9 is a graph depicting RP-HPLC measurements of SapC purity of Table 8 compositions at t=0 and after 10 days at 60° C.

FIG. 9 is a graph depicting RP-HPLC measurements of SapC purity of Table 8 compositions at t=0 and after 10 days at 60° C. All compositions exhibited decreased SapC purity after 10 days by this measure.

Figure 10:
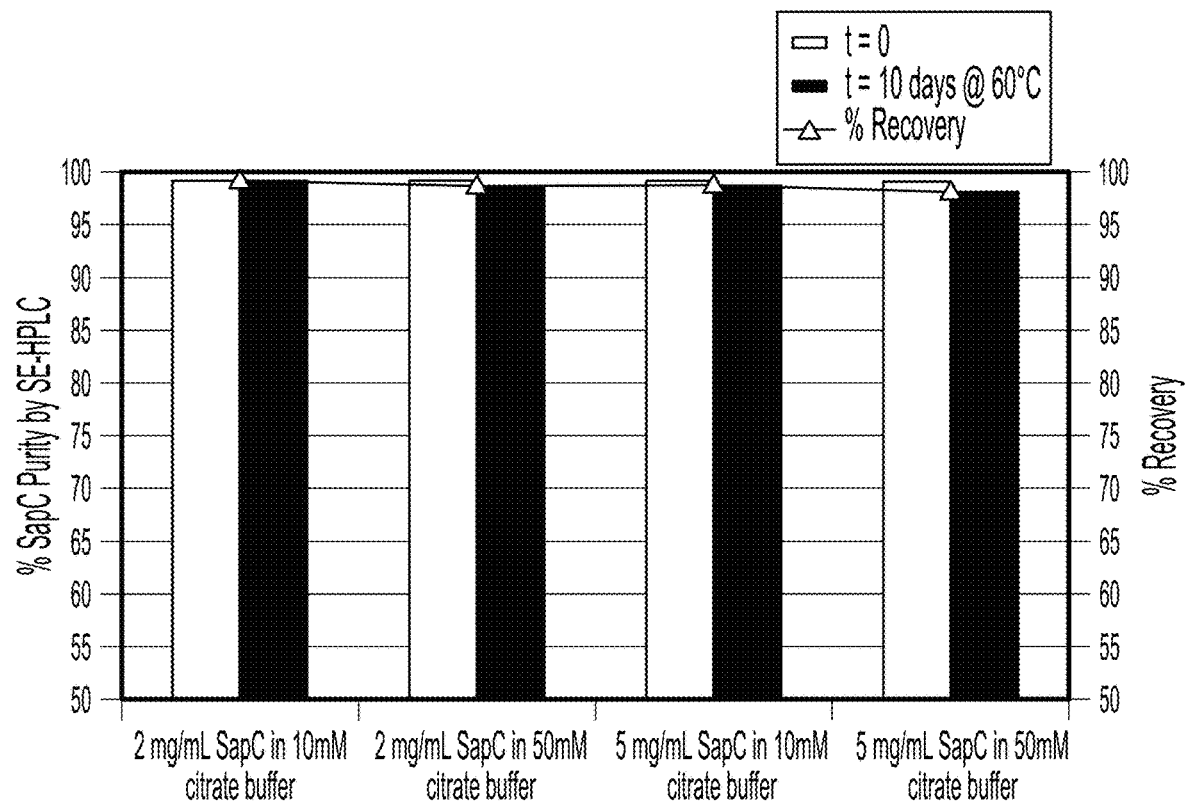
FIG. 10 is a graph depicting SE-HPLC measurements of SapC purity of Table 8 compositions at t=0 and after 10 days at 60° C.

FIG. 10 is a graph depicting SE-HPLC measurements of SapC purity of Table 8 compositions at t=0 and after 10 days at 60° C. All compositions exhibited no marked changes for SapC purity after 10 days.

Figure 11:
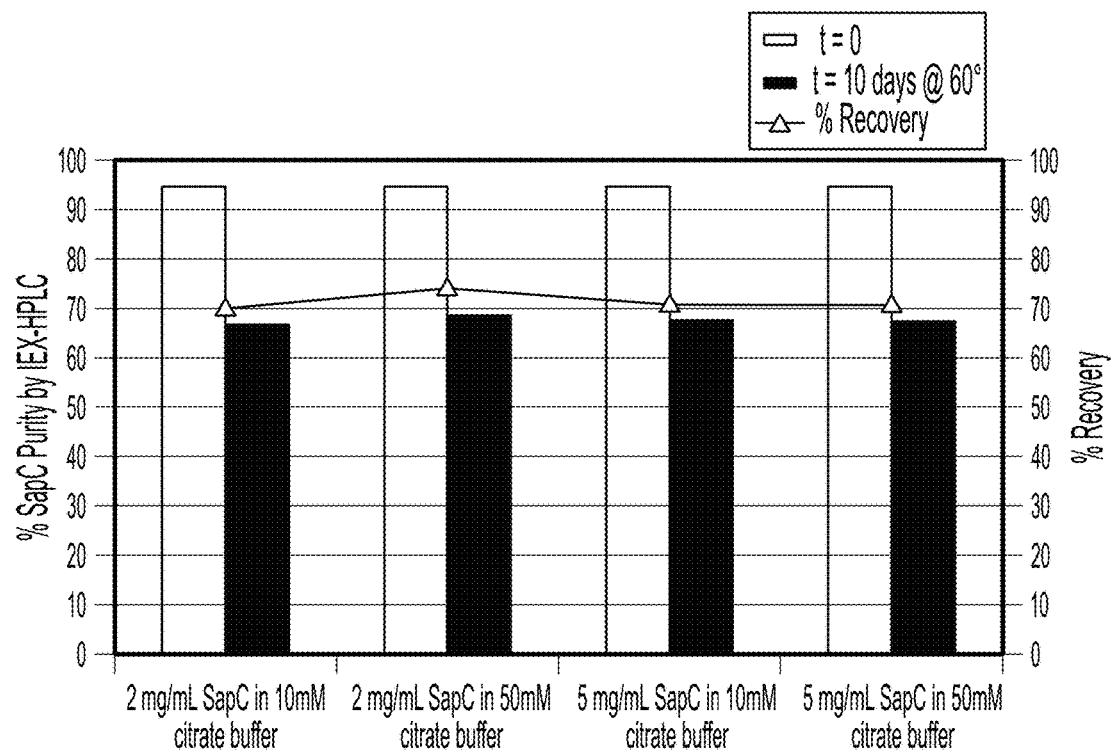
FIG. 11 is a graph depicting IEX-HPLC measurements of SapC purity of Table 8 compositions at t=0 and after 10 days at 60° C.

FIG. 11 is a graph depicting IEX-HPLC measurements of SapC purity of Table 8 compositions at t=0 and after 10 days at 60° C. All samples exhibited decreased SapC purity after 10 days by this measure.

In sum, these data indicate that samples comprising either 2 or 5 mg/mL SapC and either 10 or 50 mM citrate at a target pH of pH 6.2 (actual pH up to 6.64) exhibited similar stability and purity over 10 days at 60° C. Based on this data and the data of previous Examples, potential buffering agents for compositions comprising SapC include, but are not limited to, citrate at an approximate pH of 6.2 and Tris at an approximate pH of 7.6.

Example 4. Determination of Stability of Compositions Comprising SapC and 25 mM Tris pH 7.2 Following Exposure to Either Mechanical or Thermal Stress To quantify the stability of compositions comprising SapC and 25 mM Tris pH 7.2 following exposure to mechanical or thermal stress, the compositions were exposed to mechanical or thermal stress and analyzed by visual appearance, pH, and total protein content.

Methods

Composition 183-001-01-220-F1 comprising 5 mg/mL SapC, 25 mM Tris pH 7.1-7.2 was prepared, and samples of it were exposed either to freeze-thaw stress or to agitation stress. For each sample, the following properties were assayed as described in Example 2: visual appearance, pH, and total protein content.

For freeze-thaw stress testing, samples were divided into 1.3 mL aliquots in 5 mL PETG vials and were subjected to five freeze-thaw cycles. For each cycle, the vials were frozen at −70° C. and thawed to room temperature. After each thaw, the contents of each vial were mixed by gently inverting approximately 5 times before being returned to −70° C. for the next cycle.

For agitation stress testing, samples were divided into 1.3 mL aliquots in eight PETG vials. Four of the vials were agitated on an orbital shaker (Thermo Scientific, Model #2309) at 220 RPM for 15 or 24 hours at ambient temperature. In parallel, the remaining four vials were placed on the bench top near the shaker as stationary controls. At 15 and 24 hours, two vials from the test group and two from the control group were analyzed.

Results

All of the samples were clear and colorless liquids (data not shown).

Figure 12:
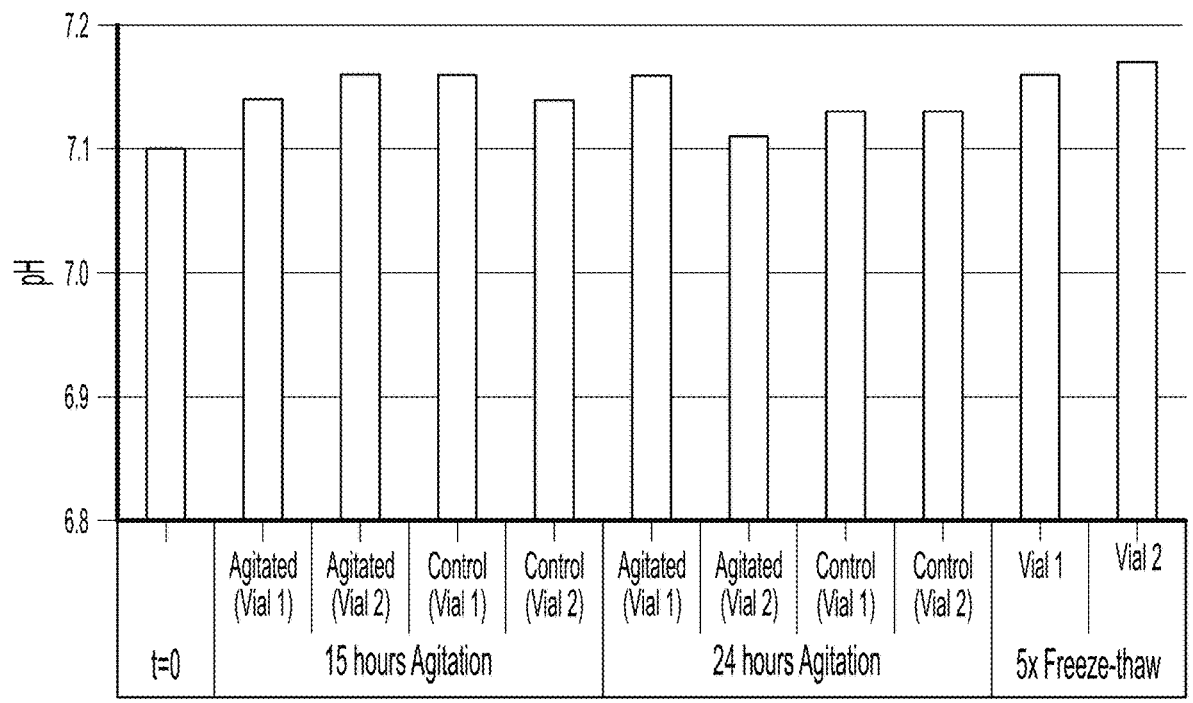
FIG. 12 is a graph depicting the pH of each sample in Example 4.

The pH of each sample is reported in FIG. 12. The pH of all samples was maintained within 0.1 pH units of the initial pH value.

Figure 13:
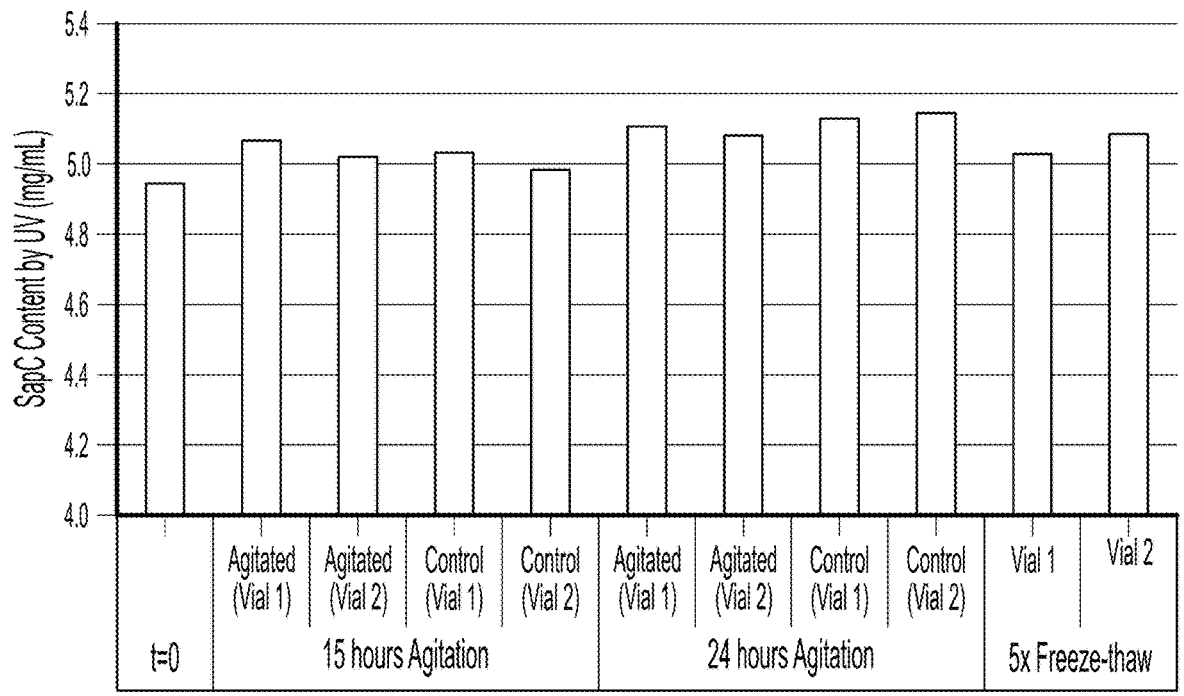
FIG. 13 is a graph depicting the protein content of each sample in Example 4.

The total protein content in each of samples is reported in FIG. 13. Protein content of all stressed samples was within 3 percent of total protein content in the unstressed sample at t=0.

In sum, the tested compositions comprising SapC and 25 mM Tris pH 7.1 (actual pH was 7.1 at t=0; target pH was 7.2) exhibited stability following exposure to mechanical or thermal stress as assessed by visual appearance, pH, and total protein content.

Example 5. Determination of how Various Concentrations of t-Butanol (TBA) Affect the Stability and Purity of Compositions Comprising SapC and Dioleoyl Phosphatidylserine (DOPS)

T-butanol (or t-butyl alcohol; TBA) was used as an organic solvent to dissolve DOPS prior to incorporating DOPS into various SapC compositions. To determine how various concentrations of TBA affect stability and purity of compositions comprising SapC, compositions comprising the concentrations of TBA listed in Table 10 were prepared, filtered, and analyzed for visual appearance, total protein content, and DOPS content.

Methods

The compositions listed in Table 10 were prepared and assessed before and after standard sterile filtration through a 0.2 micron filter. All percentages are w/w. The visual appearance and total protein content in each composition were assayed as described in Example 2. The total DOPS content in each composition was assayed by HPLC in conjunction with evaporative light scattering detector (HPLC-ELSD).

TABLE 10

Compositions containing TBA

| UID | Description |
|---|---|
| 183-001-01-050-F1 | 2.3 mg/mL SapC, SapC: DOPS molar ratio of 1:12, 9 percent trehalose, 30 percent TBA, 50 mM Tris pH 7.2 |
| 183-001-01-050-F2 | 2.3 mg/mL SapC, SapC: DOPS molar ratio of 1:12, 9 percent trehalose, 25 percent TBA, 50 mM Tris pH 7.2 |
| 183-001-01-050-F3 | 2.3 mg/mL SapC, SapC: DOPS molar ratio of 1:12, 9 percent trehalose, 20 percent TBA, 50 mM Tris pH 7.2 |

TABLE 10-continued

Compositions containing TBA

| UID | Description |
|---|---|
| 183-001-01-050-F4 | 2.3 mg/mL SapC, SapC: DOPS molar ratio of 1:12, 9 percent trehalose, 15 percent TBA, 50 mM Tris pH 7.2 |

Results

The visual appearance of each sample is described in Table 10. All of the samples were clear and colorless liquids both before and after filtration.

TABLE 11

Visual appearance each sample before and after filtration

| UID | Before filtration | After filtration |
|---|---|---|
| 183-001-01-050-F1 | Clear, colorless, and particle free | Clear, colorless, and particle free |
| 183-001-01-050-F2 | Clear, colorless, and particle free | Clear, colorless, and particle free |
| 183-001-01-050-F3 | Clear, colorless, and particle free | Clear, colorless, and particle free |
| 183-001-01-050-F4 | Clear, colorless, and particle free | Clear, colorless, and particle free |

The total protein content of each sample is reported in Table 12. All of the samples exhibited no significant change in protein content before and after filtration.

TABLE 12

Total protein content (mg/mL) in each composition before and after filtration

| UID | Before filtration | After filtration |
|---|---|---|
| 183-001-01-050-F1 | 2.25 | 2.3 |
| 183-001-01-050-F2 | 2.59 | 2.55 |
| 183-001-01-050-F3 | 2.21 | 2.26 |
| 183-001-01-050-F4 | 2.49 | 2.51 |

The total DOPS content in each sample is reported in Table 13. The compositions exhibited no significant change in DOPS content before and after filtration.

TABLE 13

Total DOPS content (mg/mL) in each composition before and after filtration

| UID | Before filtration | After filtration |
|---|---|---|
| 183-001-01-050-F1 | 3.06 | 3.10 |
| 183-001-01-050-F2 | 2.98 | 3.04 |
| 183-001-01-050-F3 | 2.97 | 2.97 |
| 183-001-01-050-F4 | 3.00 | 2.94 |

In sum, these data indicate that samples comprising 15 to 35 percent TBA exhibited similar visual appearance, protein content, and DOPS content before and after filtration.

Example 6. Determination of how Certain Excipients and Buffering Agents Affect the Stability and Purity of Compositions Comprising SapC and DOPS To determine how certain excipients and buffering agents affect stability and purity of compositions comprising SapC, the compositions listed in Table 14 were prepared, and the stability and purity of each composition was evaluated.

Methods

The compositions listed in Table 14 were prepared and 1.2 ml aliquots were lyophilized according to the lyophilization procedure described in Table 15. Each lyophilized sample was then reconstituted with 1.2 mL of HyClone™ purified water, and the lyophilized cakes were allowed to dissolve completely.

The following properties were assayed as described in Example 2: visual appearance; total protein content, and purity of protein content. The moisture content in each lyophilized sample was determined by a coulometric method. The percentage of TBA in each sample was determined by a gas chromatography coupled to mass spectrometry (GC-MS) head space method. (The TBA in the samples was what remained from the TBA used as solvent for DOPS, after sublimation of most of the TBA from the samples during the lyophilization process.)

In a further experiment, a sample of each reconstituted composition was stored at 50° C. for either 2 or 5 weeks and its stability assessed by visual appearance and purity of protein content analyzed as described in Example 2, by purity as measured using RP-HPLC, and by particle size distribution. The sizes of particles in each reconstituted liquid at t=0 and t=5 weeks were determined by dynamic light scattering using a Malvern instrument.

TABLE 14

Compositions prepared for lyophilization and reconstitution

| UID | Description |
|---|---|
| 76114-F1 | 0.4 mg/mL SapC, SapC: DOPS molar ratio of 1:12, 25 percent TBA, 9 percent sucrose, 10 mM Tris pH 8 |
| 76114-F2 | 0.4 mg/mL SapC, SapC: DOPS molar ratio of 1:12, 25 percent TBA, 9 percent trehalose, 10 mM Tris pH 8 |

TABLE 14-continued

Compositions prepared for lyophilization and reconstitution

| UID | Description |
|---|---|
| 76114-F3 | 0.4 mg/mL SapC, SapC: DOPS molar ratio of 1:12, 25 percent TBA, 4 percent mannitol, 1 percent sucrose, 10 mM Tris pH 8 |
| 76114-F4 | 0.4 mg/mL SapC, SapC: DOPS molar ratio of 1:12, 25 percent TBA, 9 percent sucrose, 10 mM Tris pH 7.2 |
| 76114-F5 | 0.4 mg/mL SapC, SapC: DOPS molar ratio of 1:12, 25 percent TBA, 9 percent trehalose, 10 mM Tris pH 7.2 |
| 76114-F6 | 0.4 mg/mL SapC, SapC: DOPS molar ratio of 1:12, 25 percent TBA, 4 percent mannitol, 1 percent sucrose, 10 mM Tris pH 7.2 |
| 76114-F7 | 0.4 mg/mL SapC, SapC: DOPS molar ratio of 1:12, 25 percent TBA, 9 percent sucrose, 10 mM histidine pH 6.5 |
| 76114-F8 | 0.4 mg/mL SapC, SapC: DOPS molar ratio of 1:12, 25 percent TBA, 8 percent trehalose, 10 mM histidine pH 6.5 |
| 76114-F9 | 0.4 mg/mL SapC, SapC: DOPS molar ratio of 1:12, 25 percent TBA, 4 percent mannitol, 1 percent sucrose, 10 mM histidine pH 6.5 |

TABLE 15

Lyophilization cycle used to prepare lyophilized compositions

| Purpose | Description |
|---|---|
| Loading | Hold at 5° C. |
| Freezing | Ramp at 0.3° C./min for 183 min; Hold at −50° C. for 60 min; Ramp at 0.3° C./min for 133 min; Hold at −10° C. for 120 min; Ramp at 0.3° C./min for 133 min; Hold −50° C. for 180 min |
| Primary drying | Hold −50° C. for 30 min at 50 mTorr; Ramp at 0.3° C./min for 67 min at 50 mTorr; Hold at −40° C. for 2400 min at 50 mTorr |
| Secondary drying | Ramp at 0.5° C./min for 120 min, 50 mTorr; Hold at 30° C. for 480 min at 50 mTorr |

Results

The visual appearance of each sample is summarized in Table 16. All of the samples containing 9 percent sucrose showed particles upon reconstitution at t=0, while all of the samples containing trehalose were particle-free—an important consideration for an injectable composition.

TABLE 16

Visual appearance of lyophilized cake and of reconstituted liquid at t = 0

| UID | Lyophilized cake | Reconstituted liquid at t = 0 |
|---|---|---|
| 76114-F1 | White fluffy, some cracking | Cloudy, particles seen; particles pelleted upon centrifugation |
| 76114-F2 | White fluffy, some cracking | Clear, colorless, particle free |
| 76114-F3 | White fluffy, some cracking | Slightly cloudy, particle free |
| 76114-F4 | White fluffy, some cracking and shrinkage | Cloudy, particles seen; particles pelleted upon centrifugation |
| 76114-F5 | White fluffy, some cracking and shrinkage | Clear, colorless, particle free |
| 76114-F6 | White fluffy, some cracking | Slightly cloudy, particle free |
| 76114-F7 | White fluffy, some cracking and shrinkage | Cloudy, particles seen; particles pelleted upon centrifugation |
| 76114-F8 | White fluffy, some cracking and shrinkage | Clear, colorless, particle free |
| 76114-F9 | White fluffy, some cracking | Clear, colorless, particle free |

The total protein content of each reconstituted composition is reported in Table 17.

TABLE 17

Total protein content (mg/mL) in each reconstituted composition at t = 0, as assessed by RP-HPLC

| UID | Total protein content (mg/mL) | Percentage recovery of SapC against theoretical |
|---|---|---|
| 76114-F1 | 0.38 | 91 |
| 76114-F2 | 0.37 | 87 |
| 76114-F3 | 0.37 | 88 |
| 76114-F4 | 0.37 | 87 |
| 76114-F5 | 0.36 | 87 |
| 76114-F6 | 0.37 | 89 |
| 76114-F7 | 0.36 | 86 |
| 76114-F8 | 0.36 | 85 |
| 76114-F9 | 0.38 | 91 |

The purity of SapC in each reconstituted composition at t=0 is reported in Table 18.

TABLE 18

SapC purity in each composition as assessed by RP-HPLC and IEX-HPLC at t = 0

| UID | Percentage SapC purity by RP-HPLC | Percentage SapC purity by IEX-HPLC |
|---|---|---|
| 76114-F1 | 93.2 | 96.1 |
| 76114-F2 | 93.2 | 95.9 |
| 76114-F3 | 93 | 96 |
| 76114-F4 | 93.6 | 96 |
| 76114-F5 | 93.5 | 95.8 |
| 76114-F6 | 93.6 | 96 |
| 76114-F7 | 93.6 | 95.8 |
| 76114-F8 | 91.8 | 95.8 |
| 76114-F9 | 93.9 | 95.9 |

The percentage of TBA in each reconstituted composition is reported in Table 19. All reconstituted compositions comprising 9 percent sucrose (F1, F4, and F7) contained higher levels of residual TBA compared to the other compositions tested.

TABLE 19

Percent TBA in each reconstituted composition at t = 0

| UID | Percent TBA |
| --- | --- |
| 76114-F1 | 2.4 |
| 76114-F2 | 1.9 |
| 76114-F3 | 0.3 |
| 76114-F4 | 2.3 |
| 76114-F5 | 1.7 |
| 76114-F6 | 0.2 |
| 76114-F7 | 2.2 |
| 76114-F8 | 1.8 |
| 76114-F9 | 0.3 |

TABLE 20

Moisture content in each lyophilized composition

| UID | Percent water at t = 0 |
| --- | --- |
| 76114-F1 | 0.3 |
| 76114-F2 | 0.4 |
| 76114-F3 | 2.1 |
| 76114-F4 | 0.4 |
| 76114-F5 | 0.3 |
| 76114-F6 | 1.1 |
| 76114-F7 | 0.4 |
| 76114-F8 | 0.3 |
| 76114-F9 | 1.0 |

Figure 14:
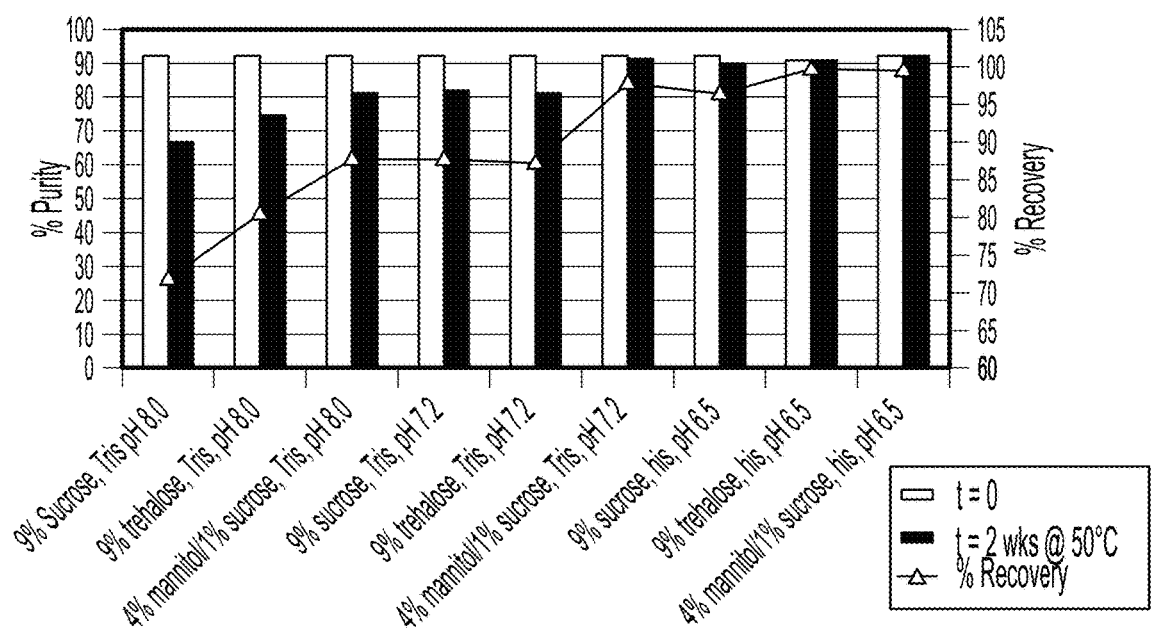
FIG. 14 is a graph depicting RP-HPLC measurements of SapC purity and percent recovery in reconstituted compositions at t=0 and after storage for 2 weeks at 50° C. for samples listed in Table 14.

FIG. 14 is a graph depicting RP-HPLC measurements of SapC purity and percent recovery in reconstituted compositions at t=0 and after storage for 2 weeks at 50° C. The purity of SapC after 2 weeks at 50° C. remained greater than 90 percent in all samples buffered with histidine at pH 6.5 (76114-F7, -F8, and -F9), as well as in the 76114-F6 sample (buffered with Tris at pH 7.2). All other samples exhibited less than 85 percent SapC purity after 2 weeks at 50° C.

The lyophilized material for samples comprising 9 percent sucrose (76114-F1, -F4, -F7) melted after 2 weeks at 50° C. (data not shown), while the other lyophilized samples did not exhibit significant changes in visual appearance after 2 weeks at 50° C.

Figure 15A:
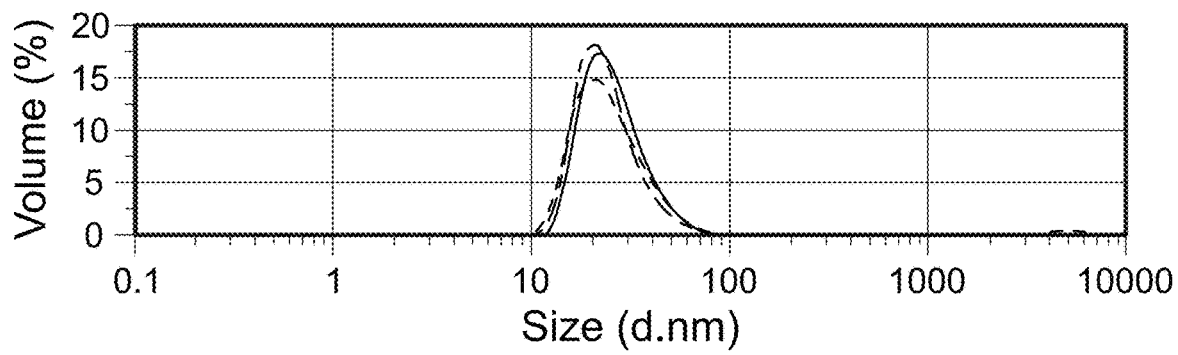
FIGS. 15A-B are graphs depicting results of dynamic light scattering for sample 76114-F5 at t=0 (A) and after 5 weeks (B) at 50° C.
Figure 15B:
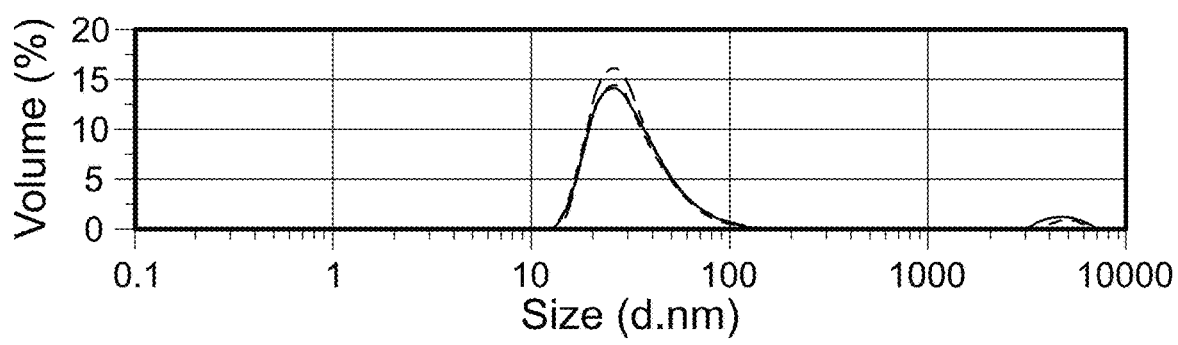
Figure 16A:
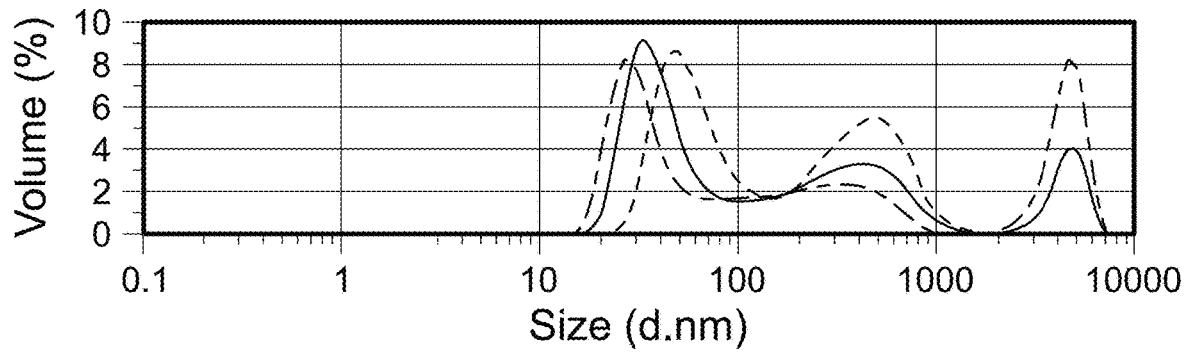
FIGS. 16A-B are graphs depicting results of dynamic light scattering for sample 76114-F6 at t=0 (A) and after 5 weeks (B) at 50° C.
Figure 16B:
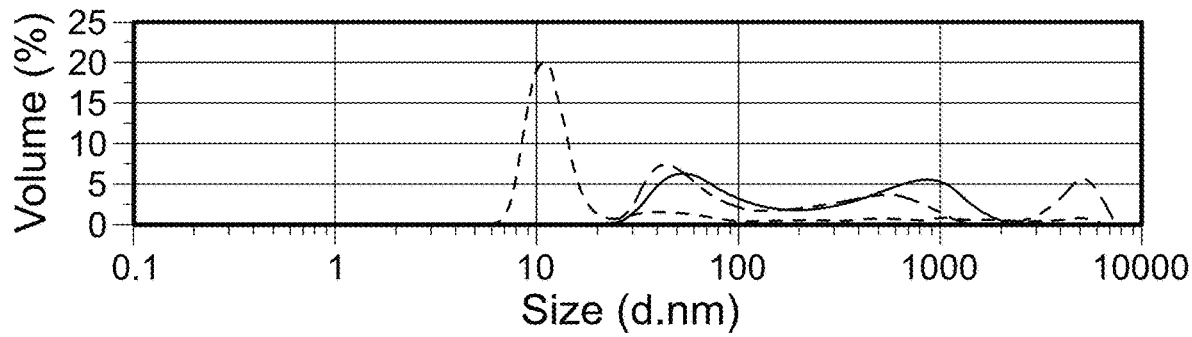

FIG. 15 is a graph depicting results of dynamic light scattering for sample 76114-F5 at t=0 (A) and after 5 weeks (B) at 50° C. FIG. 16 is a graph depicting results of dynamic light scattering for sample 76114-F6 at t=0 (A) and after 5 weeks (B) at 50° C. The compositions comprising 9 percent trehalose (F2, F5, F8) showed the most uniform and reproducible particle size volume distribution by dynamic light scattering compared to all other compositions tested.

In sum, these data suggest that trehalose is the preferred sugar excipient, compared to sucrose and to a mixture of mannitol and sucrose. This is despite the fact that compositions with mannitol/sucrose mixtures exhibited the lowest percentage TBA of all compositions tested. Additionally, these data indicate that compositions comprising SapC and DOPS are more stable in 10 mM Tris at pH 6.5 or pH 7.2 compared to in 10 mM Tris at pH 8.

Example 7: Determination of how Select Concentrations of SapC and DOPS (at a Constant SapC to DOPS Molar Ratio) Affect the Stability and Purity of Compositions Comprising SapC and DOPS To determine how various concentrations of SapC and DOPS affect stability and purity of the compositions, the compositions listed in Table 21 were prepared, and the stability and purity of each composition were evaluated.

Methods

The compositions listed in Table 21 were prepared and 1.2 ml aliquots lyophilized according to the lyophilization method described in Example 6. Each lyophilized sample was then reconstituted with 1.2 mL of HyClone™ water, and the lyophilized cakes were allowed to completely dissolve. The sizes of particles in each reconstituted sample at t=0 were determined by dynamic light scattering using a Malvern instrument.

TABLE 21

Compositions pre-lyophilization

| UID | Description |
| --- | --- |
| 76733-F1 | 4.2 mg/mL SapC, SapC:DOPS molar ratio of 1:12, 25 percent TBA, 10 mg/mL trehalose, 25 mM phosphate pH 7.4 |
| 76733-F2 | 2.2 mg/mL SapC, SapC:DOPS molar ratio of 1:12, 25 percent TBA, 10 mg/mL trehalose, 25 mM phosphate pH 7.4 |
| 76733-F3 | 1.3 mg/mL SapC, SapC:DOPS molar ratio of 1:12, 25 percent TBA, 10 mg/mL trehalose, 25 mM phosphate pH 7.4 |
| 76733-F4 | 0.82 mg/mL SapC, SapC:DOPS molar ratio of 1:12, 25 percent TBA, 10 mg/mL trehalose, 25 mM phosphate pH 7.4 |
| 76733-F5 | 0.42 mg/mL SapC, SapC:DOPS molar ratio of 1:12, 25 percent TBA, 10 mg/mL trehalose, 25 mM phosphate pH 7.4 |

Results

Figure 17:
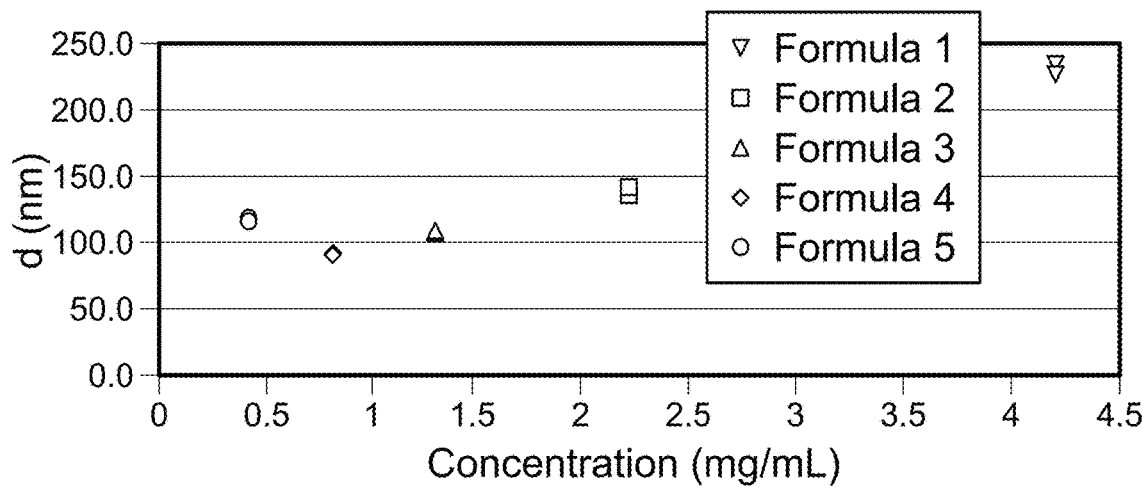
FIG. 17 is a graph depicting results of dynamic light scattering for each reconstituted sample at t=0 for samples listed in Table 21.
Figure 18:
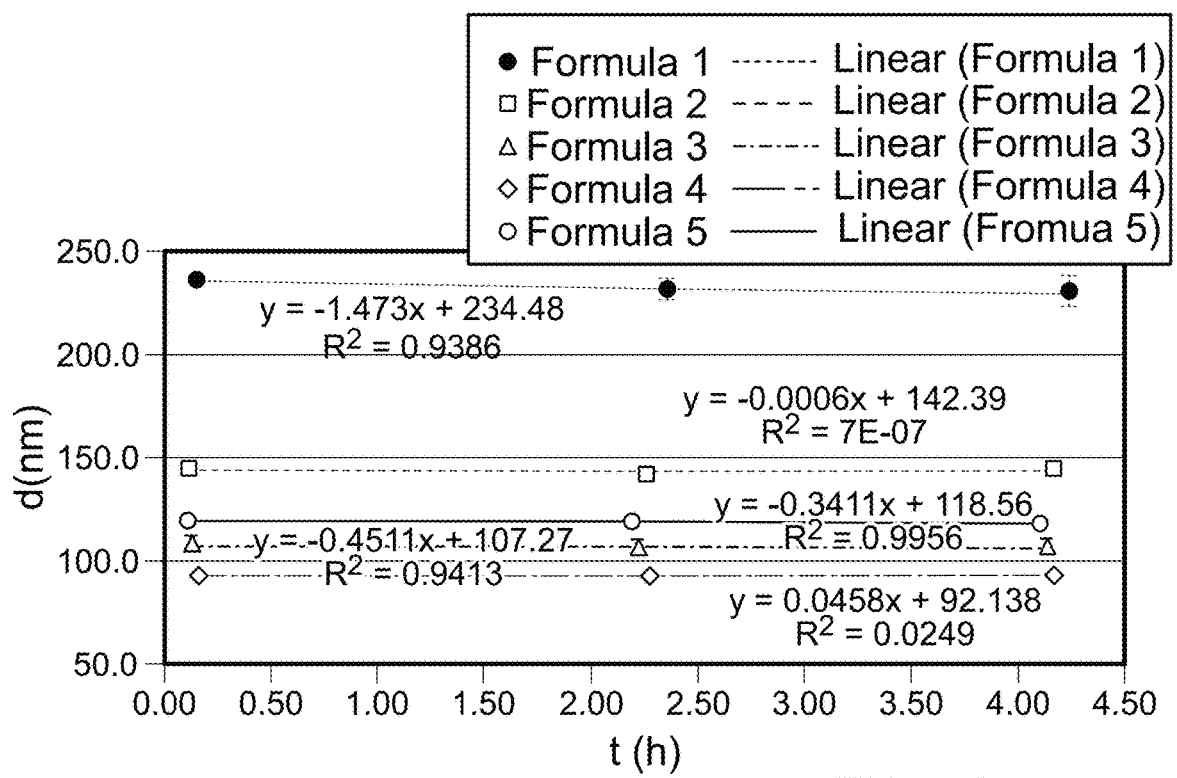
FIG. 18 is a graph depicting change in dynamic light scattering for each reconstituted sample over time for samples listed in Table 21.

FIG. 17 is a graph depicting results of dynamic light scattering for each reconstituted sample at t=0. FIG. 18 is a graph depicting change in dynamic light scattering for each reconstituted sample over time. The composition with the highest concentration of SapC, 4.2 mg/mL, showed higher average particle size relative to compositions with 2.2 mg/mL or lower concentrations of SapC. All reconstituted compositions maintained consistent average particle size over the 4 hour period, suggesting a stable reconstituted product. These results suggest that the preferred concentration of SapC is less than or equal to 2.2 mg/mL SapC, at a SapC to DOPS molar ratio of 1:12.

Example 8: Determination of how Various Concentrations of Mannitol and Trehalose Affect the Stability of Compositions Comprising DOPS To determine how various concentrations of mannitol and trehalose affect stability and purity of compositions comprising DOPS, the compositions described in Tables 22 and 23 were prepared, lyophilized, and reconstituted in water.

Methods

The compositions listed in Table 22 were prepared and 0.8 ml aliquots in 2 ml vials or 4 ml aliquots in 10 ml vials were lyophilized according to the lyophilization process described in Example 6. Each vial of lyophilized sample was reconstituted with HyClone™ water; the lyophilized cakes were allowed to completely dissolve. The visual appearance of the lyophilized cakes and the percentage of TBA in each reconstituted sample were assayed as described in Example 6.

TABLE 22

Pre-lyophilization compositions

| UID | Description |
| --- | --- |
| 81494-F1 | 1.6 mg/mL DOPS, 10 mM histidine pH 6, 1.5 percent mannitol |

TABLE 22-continued

Pre-lyophilization compositions

| UID | Description |
|---|---|
| 81494-F2 | 1.6 mg/mL DOPS, 10 mM histidine pH 6, 0.3 percent trehalose |
| 81494-F3 | 1.6 mg/mL DOPS, 10 mM histidine pH 6, 0.9 percent mannitol |
| 81494-F4 | 1.6 mg/mL DOPS, 10 mM histidine pH 6, 1.5 percent trehalose |
| 81494-F5 | 1.6 mg/mL DOPS, 10 mM histidine pH 6, 5 percent mannitol |
| 81494-F6 | 1.6 mg/mL DOPS, 10 mM histidine pH 6, 4 percent mannitol, 1 percent trehalose |
| 81494-F7 | 1.6 mg/mL DOPS, 10 mM histidine pH 6, 3 percent mannitol, 2 percent trehalose |
| 81494-F8 | 1.6 mg/mL DOPS, 10 mM histidine pH 6, 5 percent trehalose |
| 81494-F9 | 1.6 mg/mL DOPS, 10 mM histidine pH 6, 9 percent mannitol |
| 81494-F10 | 1.6 mg/mL DOPS, 10 mM histidine pH 6, 7.2 percent mannitol, 1.8 percent trehalose |
| 81494-F11 | 1.6 mg/mL DOPS, 10 mM histidine pH 6, 5.4 percent mannitol, 3.6 percent trehalose |
| 81494-F12 | 1.6 mg/mL DOPS, 10 mM histidine pH 6, 9 percent trehalose |

The compositions listed in Table 23 were prepared and lyophilized according to the lyophilization process described in Example 6, with one modification: primary drying temperature hold at −45° C. instead of hold at −40° C. Each lyophilized sample was reconstituted with 1.2 mL of HyClone™ water; the lyophilized cakes were allowed to completely dissolve. The following properties were assayed as described in Example 6: visual appearance of lyophilized cakes, percentage TBA in each reconstituted sample, and particle size distribution in each reconstituted sample.

TABLE 23

Pre-lyophilization compositions used in modified lyophilization process

| UID | Description |
|---|---|
| 183-001-01-114-F1 | 2.2 mg/mL SapC, 2.4 mg/mL DOPS, 10 mM citrate pH 6.2, 4 percent mannitol, 1 percent trehalose |
| 183-001-01-114-F2 | 2.2 mg/mL SapC, 2.4 mg/mL DOPS, 10 mM citrate pH 6.2, 3.5 percent mannitol, 1.5 percent trehalose |
| 183-001-01-114-F3 | 2.2 mg/mL SapC, 2.4 mg/mL DOPS, 10 mM citrate pH 6.2, 2 percent trehalose |
| 183-001-01-114-F4 | 2.2 mg/mL SapC, 2.4 mg/mL DOPS, 10 mM citrate pH 6.2, 7.2 percent mannitol, 1.8 percent trehalose |
| 183-001-01-114-F5 | 2.2 mg/mL SapC, 2.4 mg/mL DOPS, 10 mM citrate pH 6.2, 6.3 percent mannitol, 2.7 percent trehalose |
| 183-001-01-114-F6 | 2.2 mg/mL SapC, 2.4 mg/mL DOPS, 10 mM citrate pH 6.2, 5.4 percent mannitol, 3.6 percent trehalose |

Results

Tables 24 and 25 includes qualitative observations of the lyophilized compositions, including whether or not cake formed and if cake formed, the integrity and quality of the cake.

TABLE 24

Appearance of lyophilized cake from Table 22 compositions

| UID | Observations |
|---|---|
| 81494-F1 | No cake formed |
| 81494-F2 | No cake formed |
| 81494-F3 | No cake formed |
| 81494-F4 | No cake formed |
| 81494-F5 | No cake formed |
| 81494-F6 | No cake formed |
| 81494-F7 | Compact, fluffy cake with no cracks |
| 81494-F8 | Compact, fluffy cake with no cracks |
| 81494-F9 | Compact, fluffy cake with no cracks |
| 81494-F10 | Compact, fluffy cake with no cracks |
| 81494-F11 | Compact, fluffy cake with no cracks |
| 81494-F12 | Compact, fluffy cake with some shrinkage |

TABLE 25

Appearance of lyophilized cake from Table 23 compositions

| UID | Observations |
|---|---|
| 183-001-01-114-F1 | 4 of 4 vials exhibited compact, fluffy cake with no cracks |
| 183-001-01-114-F2 | 4 of 4 vials exhibited compact, fluffy cake with no cracks |
| 183-001-01-114-F3 | 2 of 4 vials exhibited compact, fluffy cake with no cracks |
| 183-001-01-114-F4 | 4 of 4 vials exhibited compact, fluffy cake with no cracks |
| 183-001-01-114-F5 | 3 of 4 vials exhibited compact, fluffy cake with no cracks |
| 183-001-01-114-F6 | 4 of 4 vials exhibited compact, fluffy cake with no cracks |

Figure 19:
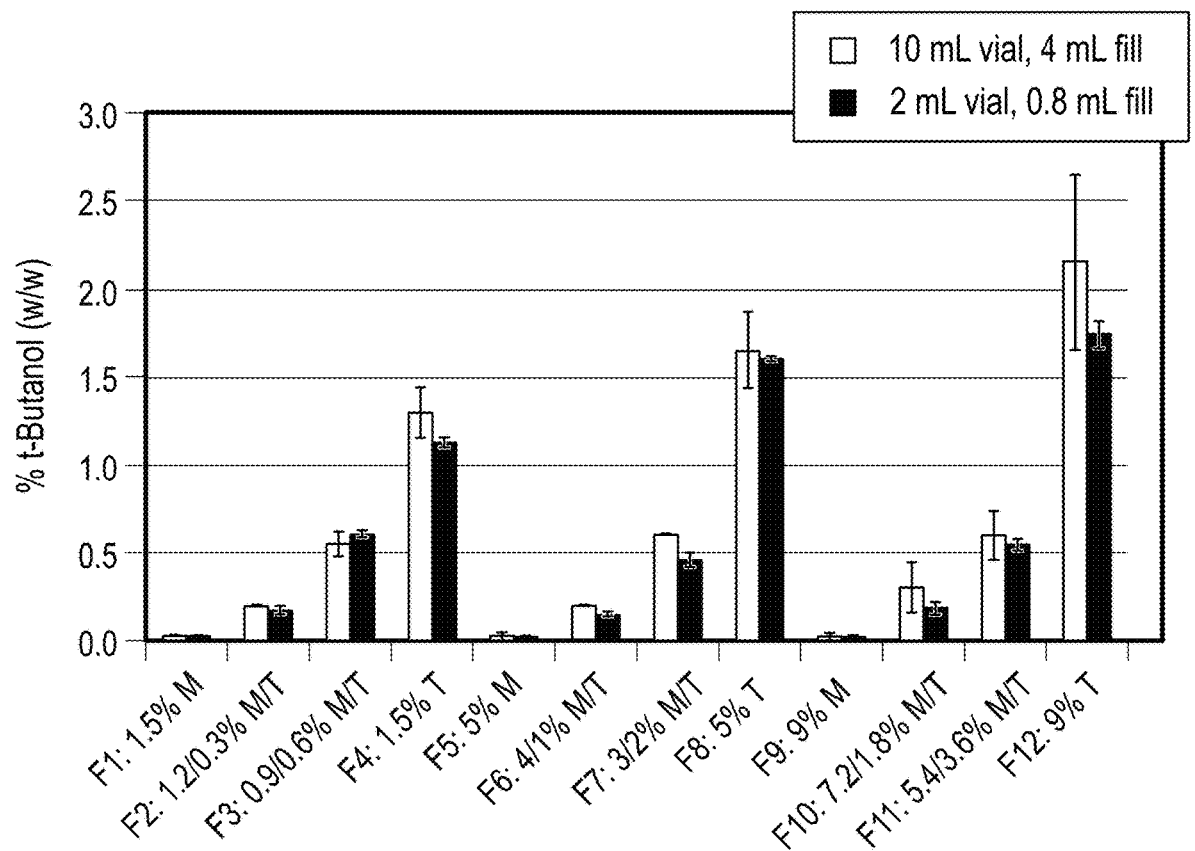
FIG. 19 is a graph depicting TBA percentage in each reconstituted sample of the Table 22 compositions.

FIG. 19 is a graph depicting TBA percentage in each reconstituted sample of the Table 22 compositions.

Figure 20:
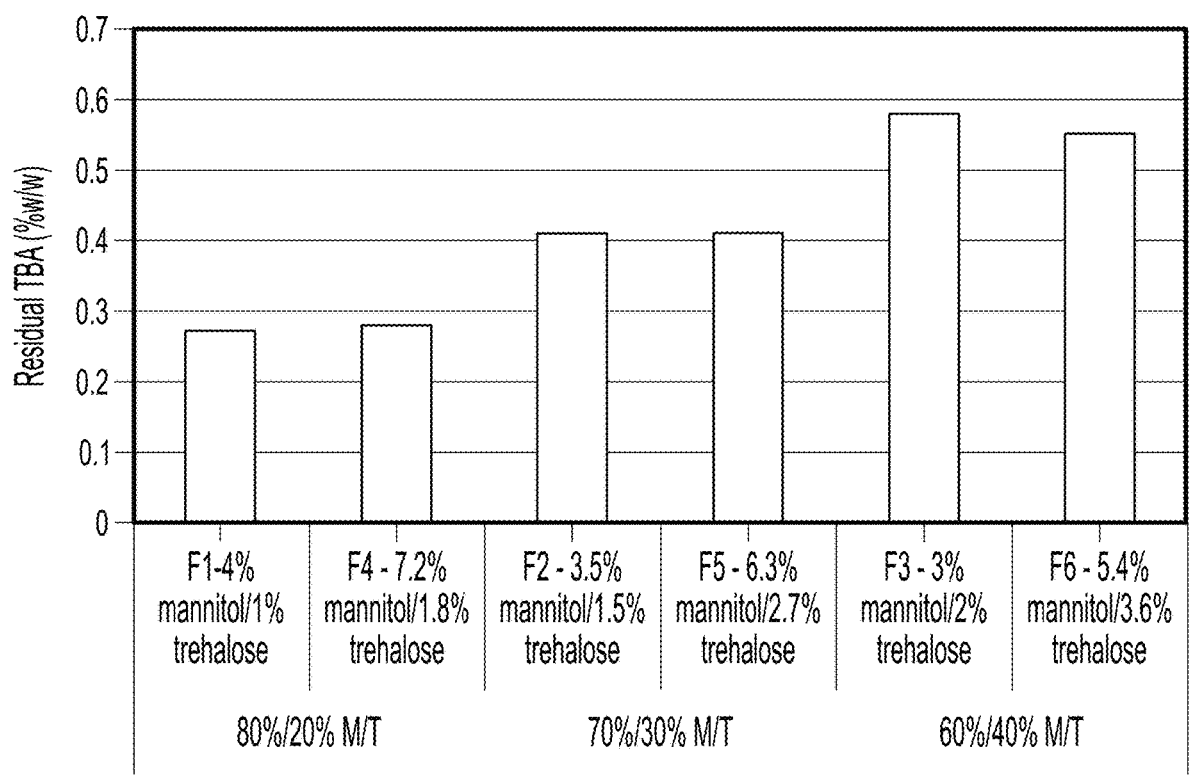
FIG. 20 is a graph depicting TBA percentage in each reconstituted sample of the Table 23 compositions.
Figure 21A:
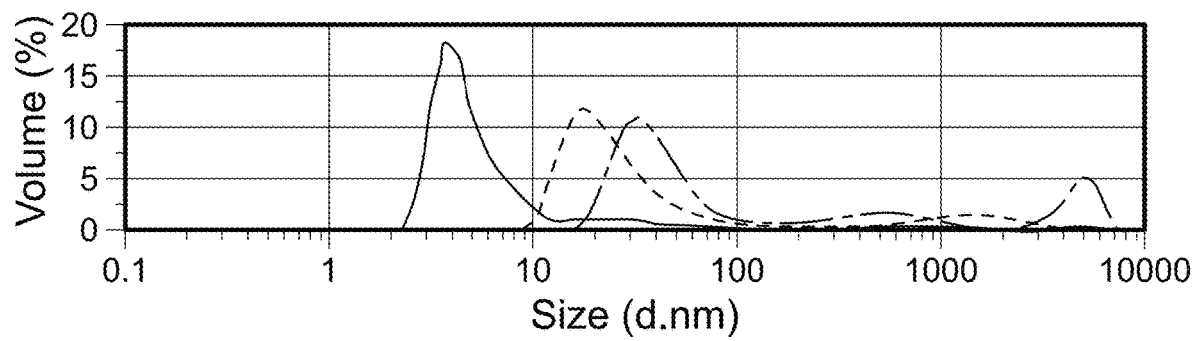
FIGS. 21A-D are graphs showing particle size distributions for three replicates of reconstituted liquids for some of the Table 23 compositions.
Figure 21B:
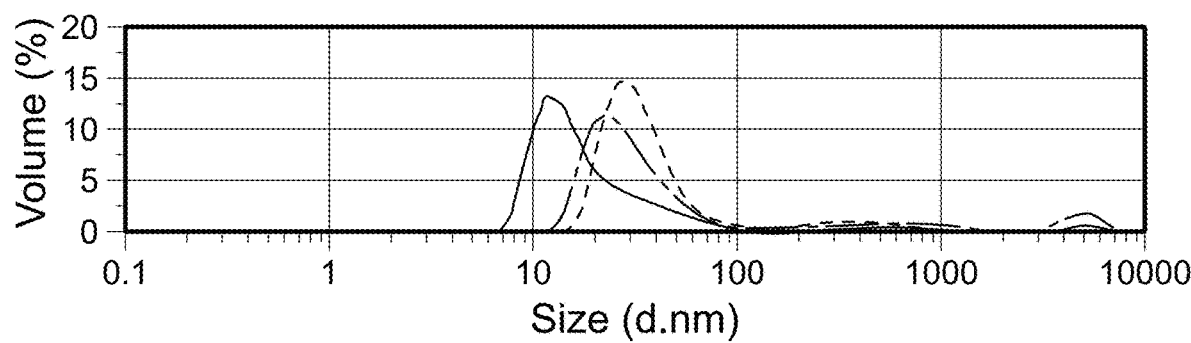
Figure 21C:
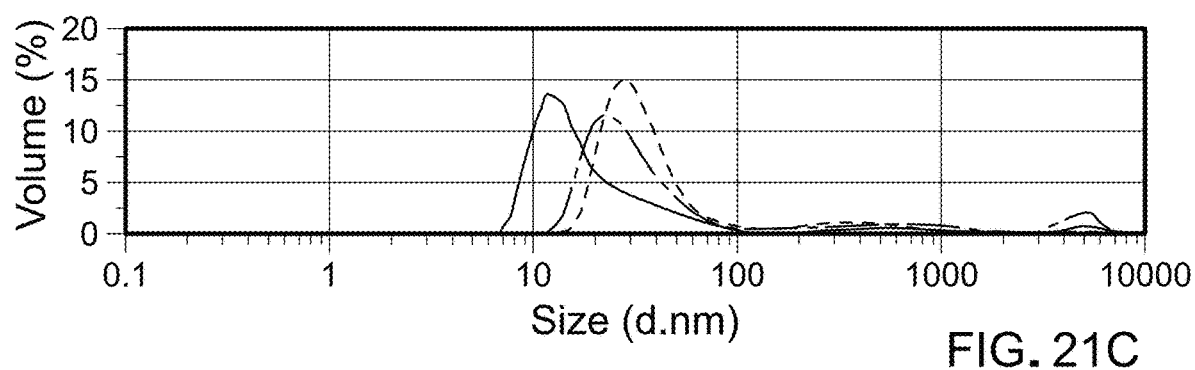
Figure 21D:
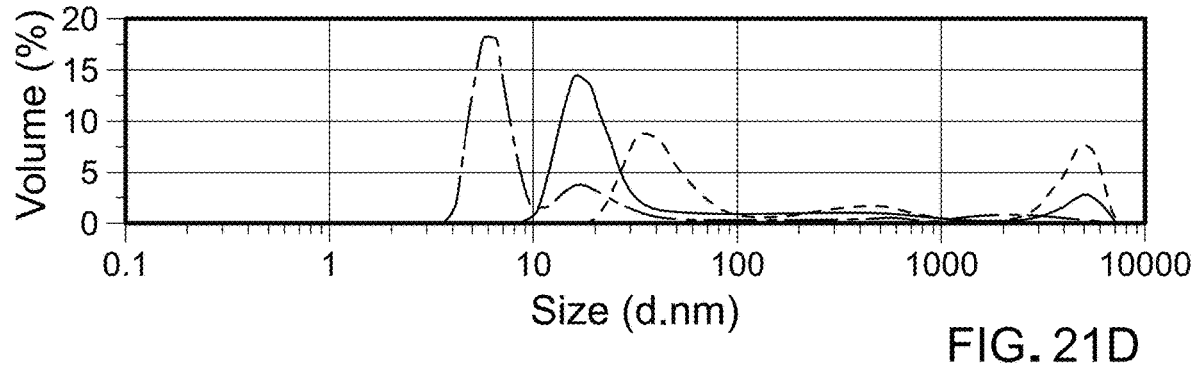

FIG. 20 is a graph depicting TBA percentage in each reconstituted sample of the Table 23 compositions.

FIG. 21 is a graph showing particle size distributions for three replicates of reconstituted liquids for the Table 23 compositions. Panel A shows data for 183-001-01-114-F1; panel B shows data for 183-001-01-114-F4; panel C shows data for 183-001-01-114-F5; and panel D shows data for 183-001-01-114-F6. A subset of the Table 22 compositions, namely 81494-F7, -F8, -F9, -F10, -F11, and -F12, formed high quality lyophilized cakes. When reconstituted in water, all six of those compositions contained less than 3 percent TBA. The reconstituted 81494-F9 and 81494-F10 compositions contained the lowest percent of TBA, at less than 0.5 percent. These data indicate that the constituents of the 81494-F7, F8, F9, F10, and F11 compositions may confer beneficial properties on both the lyophilized cake and reconstituted solution.

The quality and integrity of lyophilized cake was high for all compositions prepared with the modified lyophilization process (the Table 23 compositions), and all of those compositions, when reconstituted, had TBA levels below 0.5 percent. These results confirm previous experiments which showed that a higher percentage of mannitol correlated with a lower level of TBA in reconstituted compositions. However, compositions comprising mannitol do not exhibit as uniform and reproducible particle size distribution as has been observed for compositions comprising trehalose as the sole sugar excipient. Therefore, trehalose is the preferred sugar excipient for compositions comprising SapC and DOPS.

Example 9. Determination of how Various Compositions Affect the Stability and Purity of Compositions Comprising SapC and DOPS Based on results of previous Examples, a preferred composition for a SapC-DOPS pharmaceutical product was determined to be 2.2 mg/mL SapC, 2.4 mg/mL DOPS (SapC:DOPS molar ratio of 1:12), 25 mM Tris pH 7.2, 5 percent trehalose. To determine how varying the pH and concentrations of the components affect stability and purity of compositions comprising SapC and DOPS, the compositions listed in Table 26 were prepared and evaluated.

Method

The compositions listed in Table 26 were prepared. 4 ml aliquots were placed in vials and lyophilized according to lyophilization process described in Example 6, with one modification: the secondary drying time was 25 hours instead of 15 hours. The lyophilized cakes were stored at 50° C. for 4 weeks (or stored at 25° C. for 2 or 4 weeks) before analysis and reconstitution with 1.2 mL of HyClone™ water. The following properties were assayed as described in Example 2: visual appearance, pH, total protein content, and purity of protein content in the reconstituted samples. The following properties were assayed as described in Example 6: visual appearance of lyophilized cakes, percentage TBA in the reconstituted samples, and particle size distribution in each reconstituted sample.

TABLE 26

Compositions, pre-lyophilization

| UID | Description |
|---|---|
| 183-001-01-141-F1 | 2.2 mg/mL SapC, SapC:DOPS molar ratio of 1:12, 25 mM Tris pH 7.2, 5 percent trehalose |
| 183-001-01-141-F2 | 3.4 mg/mL SapC, SapC:DOPS molar ratio of 1:12, 25 mM Tris pH 6.8, 7.5 percent trehalose |
| 183-001-01-141-F3 | 1.0 mg/mL SapC, SapC:DOPS molar ratio of 1:12, 25 mM Tris pH 7.6, 7.5 percent trehalose |
| 183-001-01-141-F4 | 3.4 mg/mL SapC, SapC:DOPS molar ratio of 1:12, 25 mM Tris pH 7.6, 2.5 percent trehalose |
| 183-001-01-141-F5 | 1.0 mg/mL SapC, SapC:DOPS molar ratio of 1:12, 25 mM Tris pH 6.8, 2.5 percent trehalose |
| 183-001-01-141-F6 | 2.2 mg/mL SapC, SapC:DOPS molar ratio of 1:12, 25 mM Tris pH 7.2, 5 percent trehalose |
| 183-001-01-141-F7 | 2.2 mg/mL SapC, SapC:DOPS molar ratio of 1:12, 25 mM Tris pH 7.2, 5 percent trehalose |
| 183-001-01-141-F8 | 3.4 mg/mL SapC, SapC:DOPS molar ratio of 1:12, 25 mM Tris pH 7.6, 7.5 percent trehalose |
| 183-001-01-141-F9 | 1.0 mg/mL SapC, SapC:DOPS molar ratio of 1:12, 25 mM Tris pH 7.2, 2.5 percent trehalose |
| 183-001-01-141-F10 | 3.4 mg/mL SapC, SapC:DOPS molar ratio of 1:12, 25 mM Tris pH 6.8, 2.5 percent trehalose |
| 183-001-01-141-F11 | 1.0 mg/mL SapC, SapC:DOPS molar ratio of 1:12, 25 mM Tris pH 6.8, 7.5 percent trehalose |

Results

Table 27 includes qualitative observations of the lyophilized compositions stored at 50° C. for 4 weeks and of reconstituted compositions prepared from the stored lyophilized compositions and then analyzed immediately. The pH of each reconstituted sample is reported in Table 28, and the percentage TBA is shown in Table 29.

TABLE 27

Appearance of lyophilized cake stored at 50° C. for 4 weeks and appearance of reconstituted liquid prepared from the stored cake

| UID | Lyophilized cake | Reconstituted solution |
|---|---|---|
| 183-001-01-141-F1 | Compact, fluffy cake with no cracks | Slightly cloudy |
| 183-001-01-141-F2 | Compact, fluffy cake with no cracks | Slightly cloudy |
| 183-001-01-141-F3 | Compact, fluffy cake with no cracks | Clear |
| 183-001-01-141-F4 | Compact, fluffy cake with no cracks | Cloudy |
| 183-001-01-141-F5 | Compact, fluffy cake with no cracks | Slightly cloudy |
| 183-001-01-141-F6 | Compact, fluffy cake with no cracks | Slightly cloudy |
| 183-001-01-141-F7 | Compact, fluffy cake with no cracks | Slightly cloudy |
| 183-001-01-141-F8 | Compact, fluffy cake with no cracks | Slightly cloudy |
| 183-001-01-141-F9 | Compact, fluffy cake with no cracks | Slightly cloudy |
| 183-001-01-141-F10 | Compact, fluffy cake with no cracks | Cloudy |
| 183-001-01-141-F11 | Compact, fluffy cake with no cracks | Clear |

TABLE 28 pH of each reconstituted composition prepared after storing the lyophilized samples for 4 weeks

| UID | pH |
|---|---|
| 183-001-01-141-F1 | 7.2 |
| 183-001-01-141-F2 | 6.8 |
| 183-001-01-141-F3 | 7.6 |
| 183-001-01-141-F4 | 7.6 |
| 183-001-01-141-F5 | 6.8 |
| 183-001-01-141-F6 | 7.2 |
| 183-001-01-141-F7 | 7.2 |
| 183-001-01-141-F8 | 7.6 |
| 183-001-01-141-F9 | 7.6 |
| 183-001-01-141-F10 | 6.8 |
| 183-001-01-141-F11 | 6.8 |

TABLE 29

Percentage TBA in each reconstituted composition prepared after storing the lyophilized samples for 4 weeks

| UID | Percentage TBA |
|---|---|
| 183-001-01-141-F1 | 1.85 |
| 183-001-01-141-F2 | 1.94 |
| 183-001-01-141-F3 | 1.81 |
| 183-001-01-141-F4 | 1.58 |
| 183-001-01-141-F5 | 1.62 |
| 183-001-01-141-F6 | 1.78 |
| 183-001-01-141-F7 | 1.74 |
| 183-001-01-141-F8 | 1.92 |
| 183-001-01-141-F9 | 1.38 |
| 183-001-01-141-F10 | 1.44 |
| 183-001-01-141-F11 | 1.79 |

Figure 22:
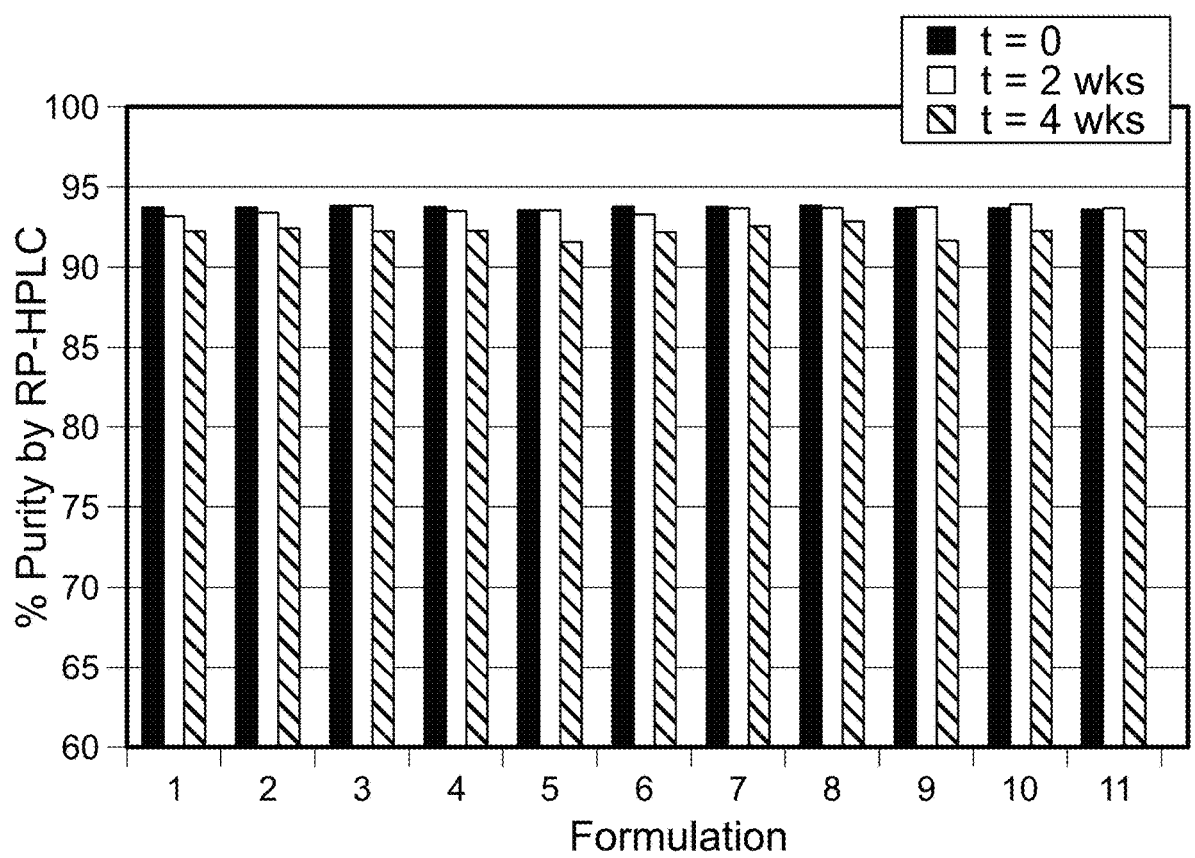
FIG. 22 is a graph depicting RP-HPLC measurements of SapC purity in each reconstituted composition prepared from lyophilized powder that had been stored at 25° C. for 2 or 4 weeks, for samples listed in Table 26.

FIG. 22 is a graph depicting RP-HPLC measurements of SapC purity in each reconstituted composition prepared from lyophilized powder that had been stored at 25° C. for 2 or 4 weeks.

Figure 23:
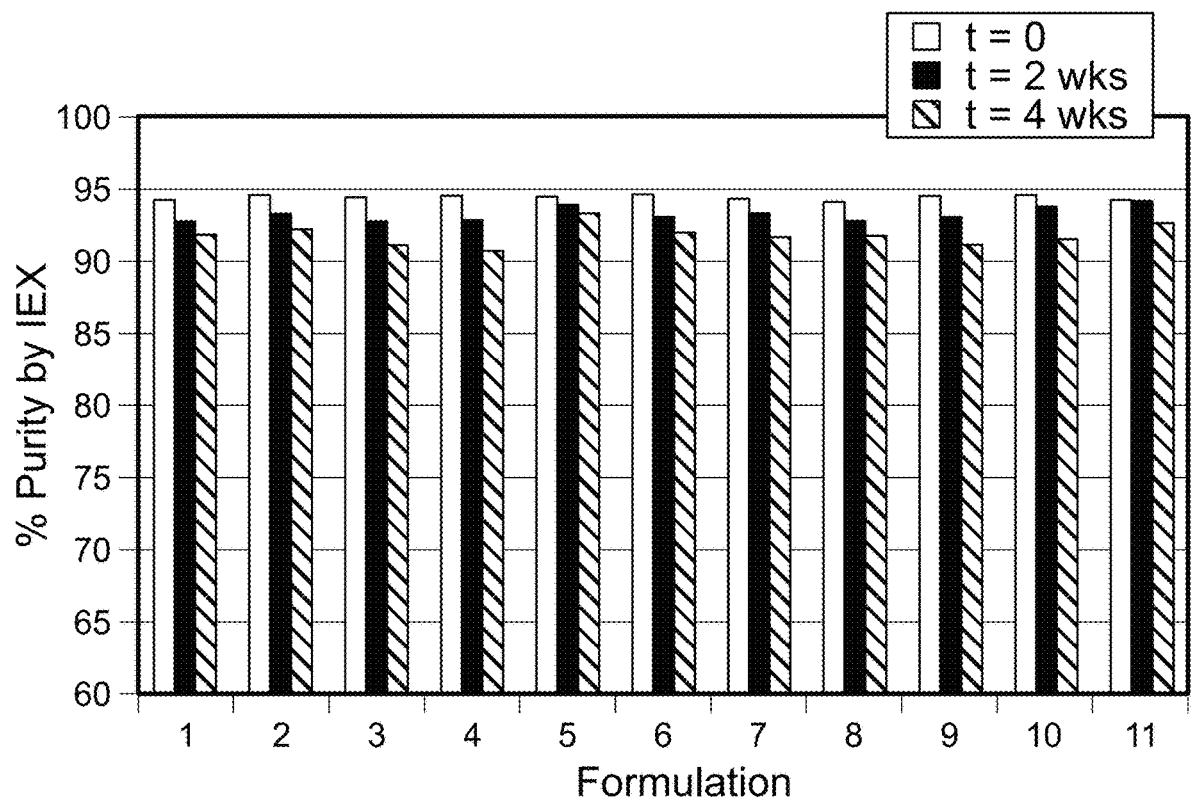
FIG. 23 is a graph depicting IEX-HPLC measurements of SapC purity in each reconstituted composition prepared from lyophilized powder that had been stored at 25° C. for 2 or 4 weeks, for samples listed in Table 26.

FIG. 23 is a graph depicting IEX-HPLC measurements of SapC purity in each reconstituted composition prepared from lyophilized powder that had been stored at 25° C. for 2 or 4 weeks.

Figure 24:
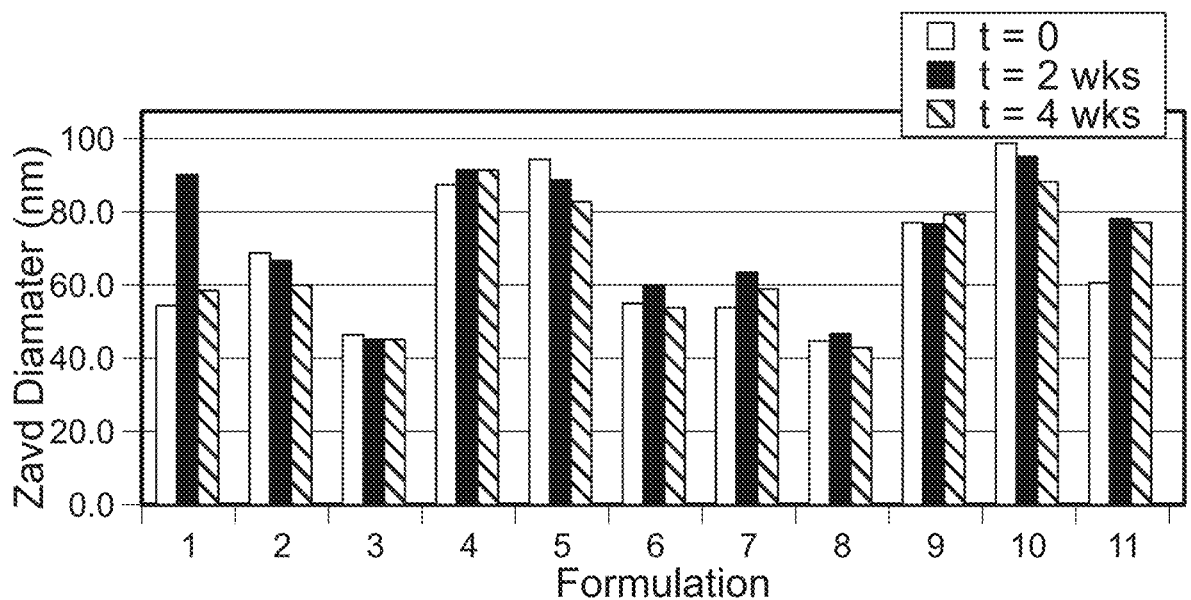
FIG. 24 is a graph depicting average particle size over time in each reconstituted composition prepared from lyophilized powder that had been stored at 25° C. for 2 or 4 weeks, for samples listed in Table 26.

FIG. 24 is a graph depicting average particle size over time in each reconstituted composition prepared from lyophilized powder that had been stored at 25° C. for 2 or 4 weeks.

The above data regarding the Table 26 compositions indicate:

(1) lyophilized cakes of all compositions reconstituted almost immediately upon addition of the diluent;
(2) appearance of all lyophilized compositions remained unchanged after 4 weeks storage at 50° C.;
(3) appearance of reconstituted products showed a composition containing 2.2 mg/mL SapC, DOPS in an amount yielding a SapC:DOPS molar ratio of 1:12, 25 mM Tris pH 7.2, and 5 percent trehalose (the preferred composition) to have acceptably low haziness;
(4) pH remained stable in all reconstituted compositions held at 50° C. for 2 or 4 weeks;
(5) reconstituted compositions with lower percentage trehalose had lower percentage TBA;
(6) average residual TBA of the preferred composition (n=3; F1, F6 and F7) after reconstitution was 1.8 percent;
(7) compositions with higher percentage trehalose exhibited lower average particle size and compositions.

Based on all data from Examples 1-9, a composition comprising a molar ratio of phosphatidylserine lipid to polypeptide in the range of 8:1 to 20:1, Tris buffer, trehalose, and TBA provided the preferred physical and chemical properties of a clinical composition.

Example 10. Evaluation of Activity of Compositions Comprising SapC and DOPS

Saposin C is known to activate the enzyme glucocerebrosidase (GBA) to catalyze the hydrolysis of cerebroside into ceremide and glucose. To test this function of the SapC-DOPS compound in vitro, recombinant human GBA enzyme (R&D Systems, cat #:7410-GHB-020) is used and, in lieu of cerebroside, 4-methylumbelliferyl-β-D-glucopyranoside, or 4-MUG, (Sigma, cat #:M3633) is used as the substrate. SapC-DOPS will activate rhGBA to cleave 4-MUG into 4-methylumbellierone (4-MU), which gives off a fluorescent signal, and glucose.

In the example below, the positive control sample was found to have 102% relative potency of the reference (REF) standard. Of note, a passing result of this assay is 70-160% relative potency. A specificity (SPEC) sample was also tested to show decreased activity if the SapC is damaged in some way. The SPEC sample contained SapC treated at 70° C. for 48 hours, then compounded with DOPS. Relative potency was unable to be determined for the SPEC sample because the curves are deemed to be different. However, the top of the best-fit curve of the SPEC sample was 79% of the top of the best-fit curve of the REF sample. A passing result for specificity is <90%. In addition, controls were utilized that include different combinations of some but not all of the critical components of the assay. Notable among these are: enzyme plus substrate without SapC-DOPS (GBA+4MU), enzyme plus substrate plus DOPS, without SapC (DOPS only), and enzyme plus substrate plus SapC without DOPS (SapC only). None of these controls produced a significant fluorescent signal, showing that both SapC and DOPS are needed to activate the enzyme to cleave the substrate.

Figure 25:
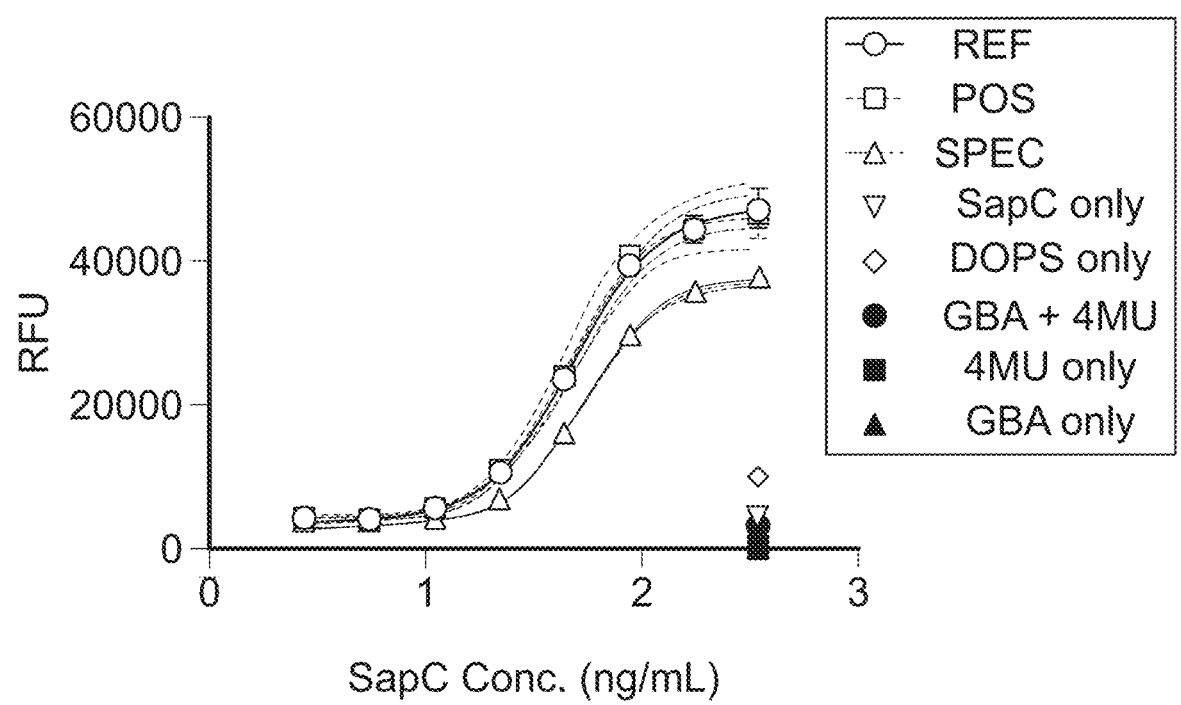
FIG. 25 is a graph showing results of a GBA enzyme assay testing activity of composition comprising SapC and DOPS.

FIG. 25 is a graph showing results of a GBA enzyme assay testing activity of SapC-DOPS.

Example 11. Protocol for Treatment with a Pharmaceutical Composition Comprising SapC and DOPS Patients 18 years of age or older with advanced solid tumors or recurrent high-grade gliomas (HGG) were enrolled in a Phase 1, open-label, dose-escalation clinical trial of a SapC/DOPS composition designated BXQ-350. The lyophilized BXQ-350 product (supplied as a lyophilized powder in a vial) is reconstituted with sterile water for injection to produce an aqueous solution containing human SapC at 2.2 mg/ml (+/−0.3 mg/ml); the sodium salt of DOPS at 2.4 mg/ml (+/−0.4 mg/ml); Tris at 25 mM (+/−2 mM), pH 7.2 (+/−0.4); trehalose at 5 percent w/v (+/−1 percent). If t-butyl alcohol is present, it is at less than 2 percent w/w.

Following a dose-escalation study, a BXQ-350 dose that delivers 2.4 mg of SapC per kg body weight was selected for further study. The administration protocol includes at least one cycle of treatment. Treatment may continue through six cycles of treatment or until disease progression, as described, for example, in Table 30. BXQ-350 is supplied as a lyophilized powder in glass vials. Prior to administration, the solid drug product is reconstituted in the vials by adding to the vial 4 mL sterile water for injection, USP, resulting in a reconstituted drug strength of 2.2 mg/mL of SapC in the vial. The reconstituted drug product is then diluted to the target IV administration concentration in sterile 0.9% saline in IV bags. Each dose is administered by IV infusion over a time period of approximately 45 minutes±15 minutes.

TABLE 30

Administration Schedule
Administration Schedule of BXQ-350

| Cycle 1 - Week 1 | Cycle 1 - Week 2 | Cycle 1 - Weeks 3 & 4 | Cycles 2 - 6 |
| --- | --- | --- | --- |
| Days 1-5 (5 consecutive days) | Days 8, 10, & 12 (Every other day) | Days 15 & 22 (Once every 7 ± 3 days) | Days 29, 57, 85, 113, & 141 (Once every 28 ± 3 days) |

FIG. 26 is a table showing Phase 1a demographics and adverse events by dosing group. No treatment-related serious adverse events were reported.

Figure 27A:
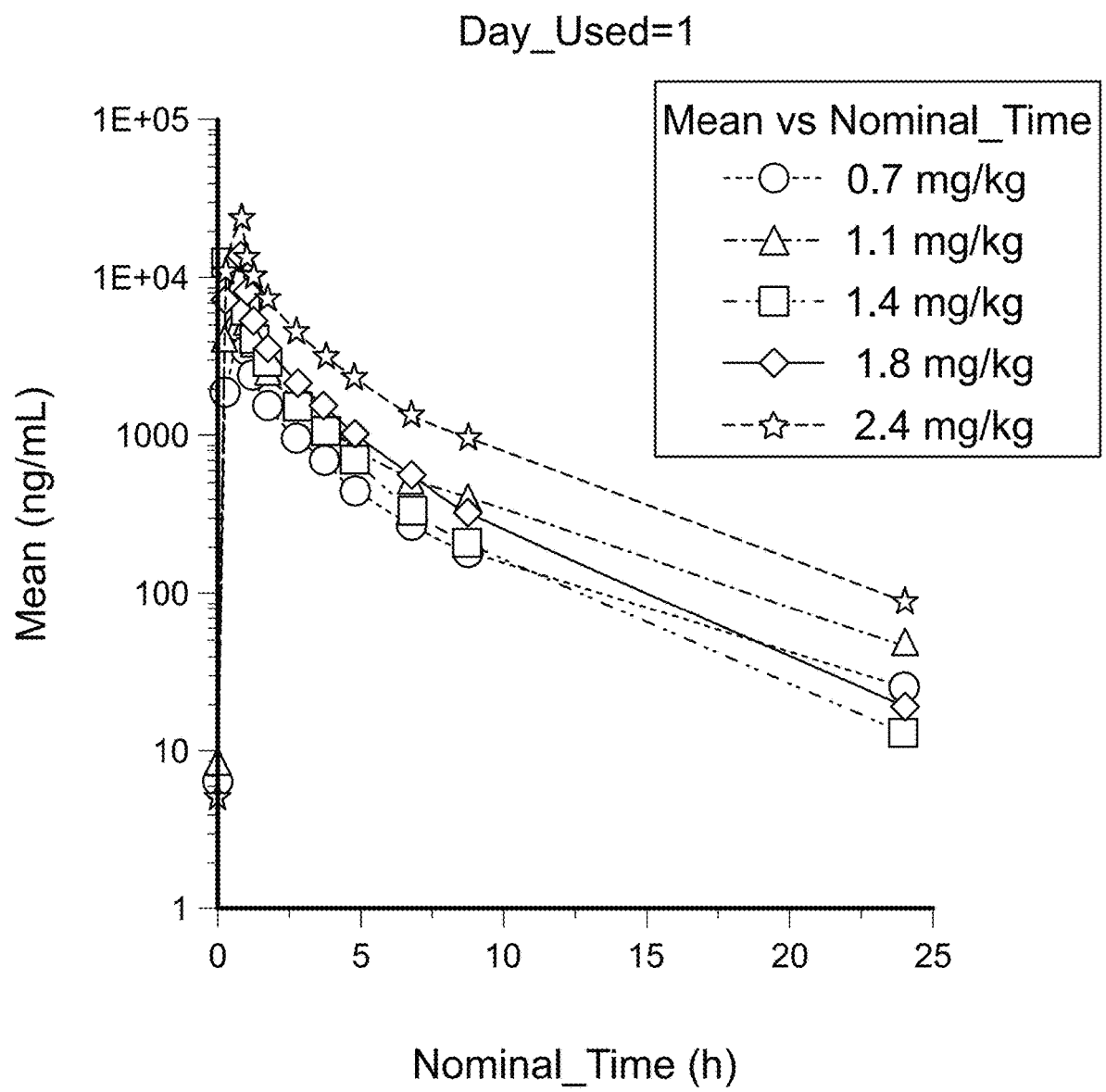
FIGS. 27A-C are three sets of graphs illustrating the mean SapC plasma concentration-time profiles upon multiple dose intravenous administration of BXQ-350 over 0.75 h every 24 hours on Day 1 (FIG. 27A), Day 4 (FIG. 27B), and Day 22 (FIG. 27C) in patients with solid tumors (log linear).
Figure 27B:
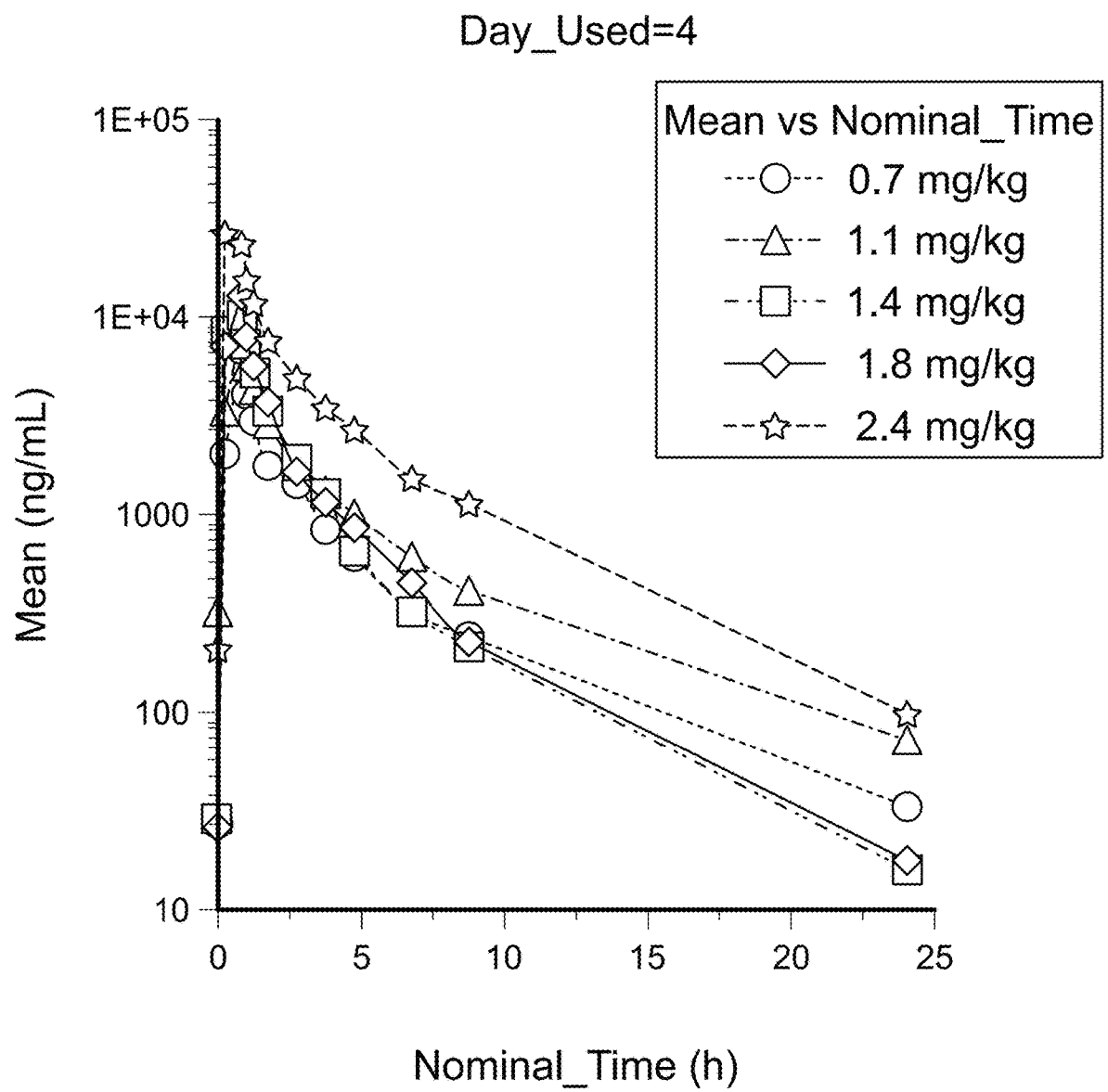
Figure 27C:
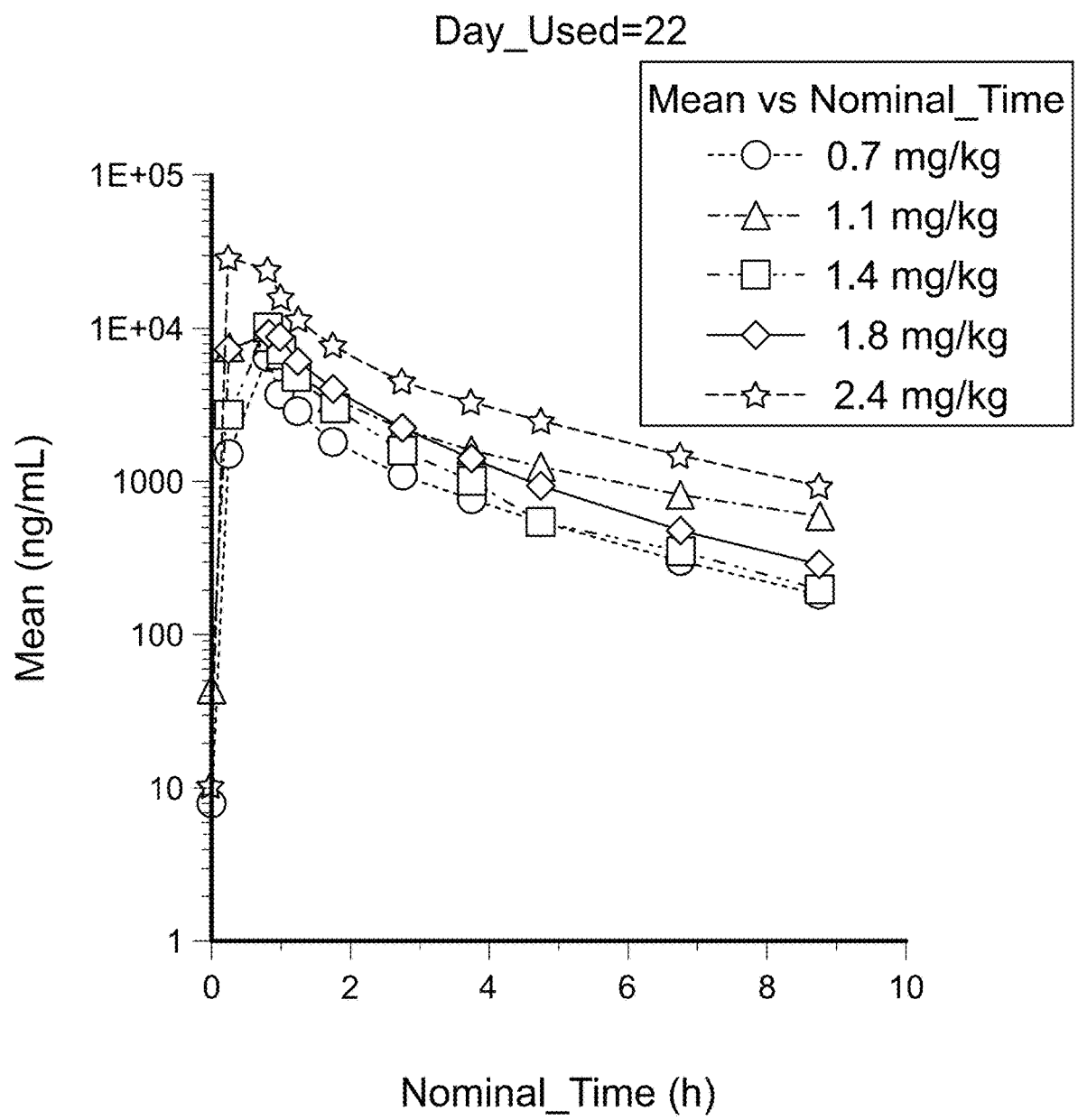

Preclinical PK/TK was allometrically scaled to predict human PK and exposure (Area Under Curve (AUC)) at 0.7-2.4 mg/kg therapeutic doses. Human clearance, terminal volume of distribution (Vz), half-life, and AUC (at 0.7-2.4 mg/kg doses) from the First In Human (FIH) trial are summarized as follows: clearance (Cl) 57-76 mL/kg/hr, Vz 314-509 mL/kg, and half-life 3.5-5 hr. The corresponding AUCs ranged from 10,020 to 42,330 hr*ng/mL. Efficacy typically occurred in murine models at doses of 4-16 mg/kg and corresponding AUCs of 7,400-29,600 hr*ng/mL. Based on mouse data, the FIH exposures fall within desired exposure range. FIGS. 27A-C are three sets of graphs illustrating the pharmacokinetic results on Day 1 (FIG. 27A), Day 4 (FIG. 27B), and Day 22 (FIG. 27C) of the Phase 1 trial. Data are presented as a semi-log plot (top of each set). Pharmacokinetics were dose-proportional.

Figure 29:
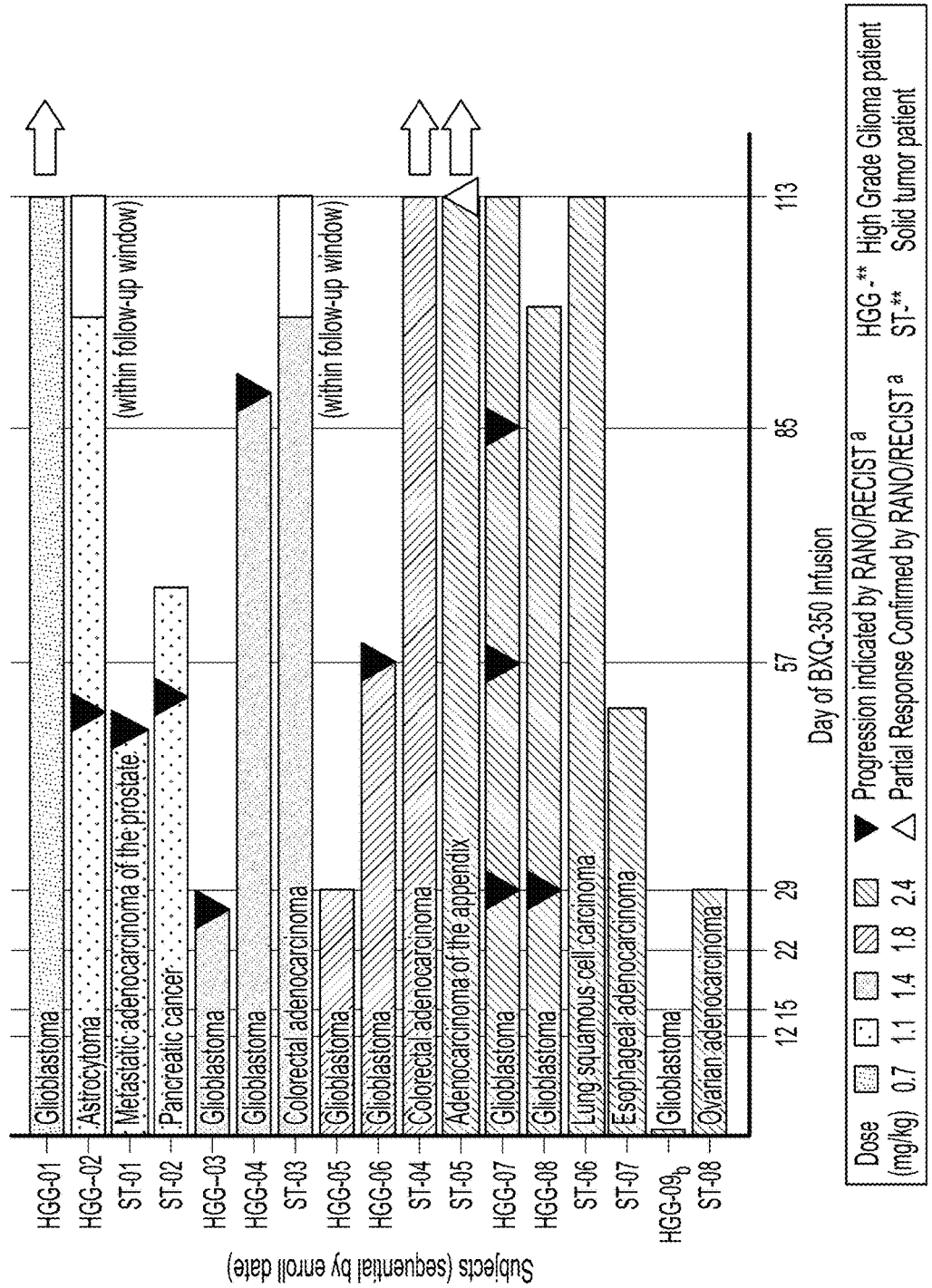
FIG. 29 is a swimmer plot illustrating patient outcomes in a Phase 1A clinical trial.

FIG. 29 is a swimmer plot illustrating patient outcomes in the Phase 1a trial. Some of the individual subjects are discussed below in Examples 12-14.

Example 12. Use of Pharmaceutical Composition Comprising SapC and DOPS to Treat a Patient Diagnosed with Parietal Anaplastic Ependymoma Methods Ependymomas are rare primary nervous system tumors accounting for about 3% of adult brain tumors in the US. Standard of care includes maximal surgical resection and radiation therapy. There is no FDA-approved drug therapy.

A 67-year old white male with a history of prostate cancer was diagnosed in October 2014 with a left parietal anaplastic ependymoma. He underwent a gross total resection, followed by adjuvant radiation. Repeat brain MRI in April 2017 showed a local recurrence. He received 3 cycles of temolozomide with no response. He was enrolled in the BXQ-350 trial in September 2017; at the time of enrollment, his Eastern Cooperative Oncology Group (ECOG) performance status was 1, and his main symptoms were aphasia and right sided-weakness. The patient received cycle 1 (BXQ-350 2.4 mg/kg IV infusion at Day 1-5, 8, 10, 12, 15, 22) and 3 additional cycles (1×28 days), and was followed until death for safety, response, Revised Assessment in Neuro-Oncology (RANO), and ECOG performance status.

Results

At baseline, the temporal lesion was 6.4×3.2 cm, associated with skull and scalp invasion. After 2 cycles, minor decrease in size of intracranial enhancing components was reported (overall stable disease per RANO). The patient received 4 total cycles of BXQ-350 without related adverse events or toxicities. Cycle 5 was withheld due to volume progression on Mill. He died 6 months post-enrollment, due to the brain tumor mass effect. Post-mortem histology and gross anatomy showed extensive brain tumor necrosis with chondroid differentiation and signs of necrotic disease in thoracic and lumbar spine on microscopy. The brain tumor necrosis observed at autopsy appeared to be treatment-related and are an indication that the drug was toxic to the tumor cells.

FIGS. 28A-D depict results from post-mortem histology and gross anatomy analysis; from left to right: (A) The initial surgical specimen showed little evidence of ependymal differentiation and abundant mitotic figures. H&E at 40×; (B) Gross brain examination at autopsy showed extensive tumor necrosis; (C) Microscopic examination of sections of tumor shows necrosis and little viable tumor (H&E at 4× with insert at 40×); (D) At autopsy there was extensive chondroid differentiation at the site where tumor extended through the surgical defect and scalp.

Example 13. Use of a Pharmaceutical Composition Comprising SapC and DOPS to Treat Patients Diagnosed with High-Grade Glioma Nine adult patients with high-grade glioma (HGG) were included in a dose-escalation trial intended to study safety of BXQ-350. The doses, given in cycles in accordance with the Table 30 protocol, ranged from 0.7 mg/kg to 2.4 mg/kg. Eight of the nine HGG patients completed a full set of cycles before withdrawal (seven due to progression; one voluntary withdrawal).

One patient with GBM completing more than six cycles (>12 months) of treatment with doses starting at 0.7 mg/kg exhibited stable disease, a decrease in lesion size, and no significant progressive functional neurological deficits. Six of the HGG patients had improved RANO/RECIST at day 113.

Example 14. Use of a Pharmaceutical Composition Comprising SapC and DOPS to Treat a Patient Diagnosed with Adenocarcinoma of the Appendix A 62-yr old female with locally advanced mucinous adenocarcinoma of the appendix was treated as part of the Phase 1a trial. Following resection and post-operative adjuvant chemotherapy (FOLFOX), a 2007 recurrence in the pelvis involving ovaries led to debulking surgery including total abdominal hysterectomy/bilateral salpingo-oopherectomy followed by systemic therapy with irinotecan and cetuximab. In 2009, recurrence led to extensive debulking surgery and intraabdominal hyperthermic perfusion, with complete remission. After declining treatment for recurrence in 2016, she started BXQ-350 in July 2017. She was given 2.4 mg/kg BXQ-350 by IV, in accordance with the phase 1 protocol and experienced a partial response, remaining on study in the Phase 1b trial after completing 11 cycles and without serious adverse events attributable to BXQ-350.

Example 15. Use of a Pharmaceutical Composition Comprising SapC and DOPS to Treat Patients Diagnosed with Rectal Adenocarcinoma Adult patients with various solid tumors were included in a dose-escalation trial intended to study safety of BXQ-350. The doses, given in cycles in accordance with the Table 30 protocol, ranged from 0.7 mg/kg to 2.4 mg/kg. All patients completed at least one cycle before withdrawal.

Figure 30A:
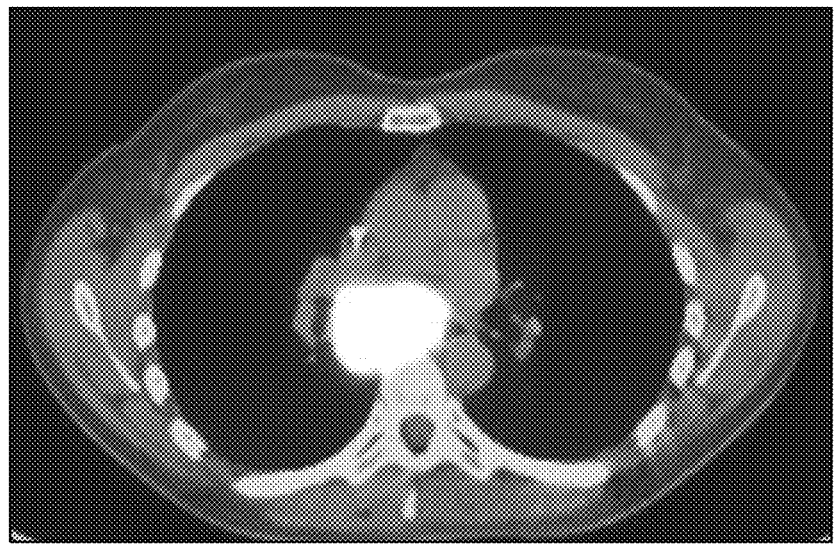
FIGS. 30A-B are a pair of positron emission tomography (PET) images at the start of treatment (FIG. 30A) and after more than 12 months of treatment (FIG. 30B).
Figure 30B:

One patient diagnosed with metastatic (Stave IV) rectal adenocarcinoma completed more than 12 months of treatment with doses starting at 1.8 mg/kg and exhibited stable disease, with evidence for significant decrease of tumor metabolic activity by positron emission tomography (PET), utilizing flurodeoxyglucose (F-18 FDG) after more than 12 months of treatment. See FIGS. 30A and 30B.

What is claimed is:

1. An in vitro method for assaying potency of a test composition comprising saposin C and an anionic phospholipid, the method comprising:
 carrying out a first assay that comprises contacting the test composition with glucocerebrosidase and 4-methylumbelliferyl-β-D-glucopyranoside (4-MUG);
 carrying out a control assay that comprises contacting a control composition with glucocerebrosidase and 4-MUG;
 determining the level of 4-methylumbellierone (4-MU) formed as a result of cleavage of 4-MUG in the first assay;
 determining the level of 4-MU formed as a result of cleavage of 4-MUG in the control assay; and
 comparing the level of 4-MU formed in the first assay to the level of 4-MU in the control assay, thereby determining the relative potency of the test composition compared to the control composition.

2. The method of claim 1, wherein the anionic phospholipid is a phosphatidylserine lipid.

3. The method of claim 1, wherein the anionic phospholipid is dioleoyl phosphatidylserine (DOPS).

4. The method of claim 3, wherein the control composition is a reference standard sample comprising saposin C and DOPS.

5. The method of claim 4, wherein the test composition is determined to have a relative potency, compared to the reference standard sample, of 70-160%.

6. The method of claim 5, wherein the test composition is a sample from a batch of SapC-DOPS prepared for pharmaceutical use, and the determination that the relative potency of the test composition is 70-160% that of the reference standard sample is one step in determining if the batch of SapC-DOPS is sufficiently potent for pharmaceutical use.

7. The method of claim 1, wherein the control composition is a negative control sample comprising partially inactivated saposin C and the anionic phospholipid.

8. The method of claim 7, wherein the anionic phospholipid in both the test composition and the negative control sample is a phosphatidylserine lipid.

9. The method of claim 7, wherein the anionic phospholipid in both the test composition and the negative control sample is DOPS.

10. The method of claim 7, wherein the partially inactivated saposin C in the negative control sample was produced by a process comprising treating a sample of saposin C with heat sufficient to partially inactivate the saposin C.

11. The method of claim 1, wherein the glucocerebrosidase is recombinant human glucocerebrosidase.

12. The method of claim 1, wherein the level of 4-MU formed in the first assay and in the control assay is determined by detecting a fluorescent signal given off by 4-MU.

13. The method of claim 1, further comprising repeating the first assay multiple times, to test different amounts of the test composition, and repeating the control assay multiple times, to test different amounts of the control composition.

14. The method of claim 13, further comprising plotting the results of the repeated first assay and the results of the repeated control assay on a graph.

15. An in vitro method for comparing potency of a test composition comprising saposin C and an anionic phospholipid to the potency of a reference standard comprising saposin C and the anionic phospholipid, the method comprising:
 carrying out a series of glucocerebrosidase/4-MUG assays comprising contacting glucocerebrosidase and 4-MUG with different amounts of the test composition;
 determining the level of 4-MU formed as a result of cleavage of 4-MUG in each assay;
 comparing 4-MU-level data from the series of assays to 4-MU-level data generated in glucocerebrosidase/4-MUG assays on the reference standard, thereby comparing potency of the test composition to the potency of the reference standard.

16. The method of claim 15, wherein the anionic phospholipid is a phosphatidylserine lipid.

17. The method of claim 15, wherein the anionic phospholipid is DOPS.

18. The method of claim 15, wherein the level of 4-MU formed in each assay is determined by detecting a fluorescent signal given off by 4-MU.

19. The method of claim 15, wherein the test composition is from a batch of SapC-DOPS prepared for pharmaceutical use, and the method is one step in determining if the batch of SapC-DOPS is sufficiently potent for pharmaceutical use.

20. The method of claim 19, wherein the potency of the test composition is determined to be between 70-160% of the potency of the reference standard, thereby meeting one criterion for determining if the batch of SapC-DOPS is sufficiently potent for pharmaceutical use.

* * * * *